(12) United States Patent
Lockwood et al.

(10) Patent No.: US 8,956,682 B2
(45) Date of Patent: Feb. 17, 2015

(54) HYDROPHILIC POLYMERIC COATINGS FOR MEDICAL ARTICLES WITH VISUALIZATION MOIETY

(71) Applicant: SurModics, Inc., Eden Prairie, MN (US)

(72) Inventors: Nathan A. Lockwood, Minneapolis, MN (US); Bruce M. Jelle, Chanhassen, MN (US); Aleksey V. Kurdyumov, Maplewood, MN (US)

(73) Assignee: Surmodics, Inc., Eden Prairie, MN (US)

( * ) Notice: Subject to any disclaimer, the term of this patent is extended or adjusted under 35 U.S.C. 154(b) by 127 days.

(21) Appl. No.: 13/855,260

(22) Filed: Apr. 2, 2013

(65) Prior Publication Data

US 2013/0261566 A1    Oct. 3, 2013

Related U.S. Application Data

(60) Provisional application No. 61/618,960, filed on Apr. 2, 2012, provisional application No. 61/740,180, filed on Dec. 20, 2012.

(51) Int. Cl.
| | |
|---|---|
| *A61L 33/00* | (2006.01) |
| *A61F 2/00* | (2006.01) |
| *A61K 9/14* | (2006.01) |
| *B05B 5/00* | (2006.01) |
| *A01N 35/00* | (2006.01) |
| *A61K 31/12* | (2006.01) |
| *C09D 5/22* | (2006.01) |
| *C09D 5/00* | (2006.01) |
| *B05D 3/06* | (2006.01) |
| *A61L 29/08* | (2006.01) |
| *A61L 29/14* | (2006.01) |
| *A61L 29/18* | (2006.01) |

(52) U.S. Cl.
CPC .. *C09D 5/22* (2013.01); *C09D 5/00* (2013.01); *B05D 3/067* (2013.01); *A61L 29/085* (2013.01); *A61L 29/14* (2013.01); *A61L 29/18* (2013.01); *A61L 2420/02* (2013.01)
USPC .......... 427/2.24; 427/157; 424/423; 424/484; 514/686

(58) Field of Classification Search
CPC ............ A61L 2420/02; A61L 2420/06; A61L 2420/09; A61L 31/10; A61L 27/34; A61L 29/085; A61L 27/50; A61L 29/14; A61L 31/14
USPC ........... 427/2.24, 157; 424/423, 484; 514/686
See application file for complete search history.

(56) References Cited

U.S. PATENT DOCUMENTS

| | | | |
|---|---|---|---|
| 5,002,582 A | 3/1991 | Guire et al. | |
| 5,414,075 A | 5/1995 | Swan et al. | |
| 5,563,056 A | 10/1996 | Swan et al. | |
| 5,637,460 A | 6/1997 | Swan et al. | |
| 5,714,360 A | 2/1998 | Swan et al. | |
| 5,807,605 A | 9/1998 | Tingey et al. | |
| 5,821,287 A | 10/1998 | Hu et al. | |
| 5,858,653 A | 1/1999 | Duran et al. | |
| 6,156,345 A | 12/2000 | Chudzik et al. | |
| 6,211,374 B1 | 4/2001 | Ippoliti | |
| 6,278,018 B1 | 8/2001 | Swan | |
| 6,362,248 B1 | 3/2002 | Hara et al. | |
| 6,410,044 B1 | 6/2002 | Chudzik et al. | |
| 7,052,512 B2 | 5/2006 | Yang et al. | |
| 7,056,533 B2 | 6/2006 | Chudzik et al. | |
| 7,429,623 B2 | 9/2008 | Molock et al. | |
| 7,592,418 B2 | 9/2009 | Pathak et al. | |
| 7,772,393 B2 | 8/2010 | Guire et al. | |
| 7,820,072 B2 | 10/2010 | Hsieh et al. | |
| 8,349,452 B2 | 1/2013 | Jung et al. | |
| 2005/0254003 A1 | 11/2005 | Jani et al. | |
| 2006/0052460 A1* | 3/2006 | Guire et al. | .......... 514/686 |
| 2006/0287410 A1 | 12/2006 | Chudzik et al. | |
| 2007/0197750 A1 | 8/2007 | Gibanel et al. | |
| 2008/0261323 A1 | 10/2008 | Diamond et al. | |
| 2010/0198168 A1 | 8/2010 | Rooijmans et al. | |
| 2011/0046255 A1 | 2/2011 | Rooijmans et al. | |
| 2011/0059874 A1 | 3/2011 | Rooijmans et al. | |
| 2011/0144373 A1 | 6/2011 | Swan et al. | |
| 2011/0245367 A1 | 10/2011 | Kurdyumov et al. | |
| 2012/0082713 A1 | 4/2012 | Meyering et al. | |
| 2012/0149934 A1 | 6/2012 | Kurdyumov et al. | |
| 2013/0143056 A1 | 6/2013 | Swan et al. | |

FOREIGN PATENT DOCUMENTS

| | | |
|---|---|---|
| EP | 1156075 | 11/2001 |
| WO | WO 97/22037 | 6/1997 |
| WO | WO 01/02449 | 1/2001 |
| WO | WO 01/90268 | 11/2001 |
| WO | WO 03/022322 | 3/2003 |
| WO | WO 03/030879 | 4/2003 |
| WO | WO 03/061631 | 7/2003 |
| WO | WO 2004/056406 | 7/2004 |
| WO | WO 2006/119328 | 11/2006 |
| WO | WO 2007/027479 | 3/2007 |
| WO | WO 2009/112548 | 9/2009 |
| WO | WO 2010/039653 | 4/2010 |
| WO | WO 2012/006135 | 1/2012 |

OTHER PUBLICATIONS

Siegrist, A.E., et al., (2012) *Optical Brighteners*, Ullmann's Encyclopedia of Industrial Chemistry 25: 427-449.

* cited by examiner

*Primary Examiner* — Abigail Fisher
(74) *Attorney, Agent, or Firm* — Kagan Binder, PLLC

(57) ABSTRACT

The invention is directed to medical device coatings, such as coated guidewires and catheters, containing a visualization moiety providing color to the coating in ambient or applied light. The coating allows for visual or machine inspection of coating properties such as uniformity of coverage. In some embodiments the coatings include the visualization moiety and an activated UV photogroup, which is used to provide covalent bonding in the coating. The visualization moiety can be in particulate form and entrained in the coating, or can be covalently bonded to the hydrophilic polymer backbone. In other embodiments the visualization moiety includes a stilbene chemical group. Exemplary coatings include a hydrophilic vinyl pyrrolidone polymer, which can provide lubricity to the device surface, along with the colored properties.

12 Claims, 3 Drawing Sheets iron (III) oxide        iron ferrocyanide

HYDROPHILIC POLYMERIC COATINGS FOR MEDICAL ARTICLES WITH VISUALIZATION MOIETY

CROSS-REFERENCE TO RELATED APPLICATION

The present non-provisional application claims the benefit of commonly owned provisional application having Ser. No. 61/618,960, filed on Apr. 2, 2012, entitled HYDROPHILIC POLYMERIC COATINGS FOR MEDICAL ARTICLES, and commonly owned provisional application having Ser. No. 61/740,180, filed on Dec. 20, 2012, entitled HYDROPHILIC POLYMERIC COATINGS FOR MEDICAL ARTICLES, which applications are incorporated herein by reference in their entirety.

FIELD

The invention relates to hydrophilic polymeric coatings for surfaces of medical articles and hydrophilic polymer coatings that can be visualized with light.

BACKGROUND

Biocompatible polymers have been used to prepare polymeric matrices that can be associated with, or formed into, implantable medical devices. For example, biocompatible polymers can be used to make a coating on the medical device's surface.

Polymeric surface coatings can provide medical articles, such as those that are implanted or temporarily inserted into the body, with a variety of distinct benefits. These benefits include lubricity and wettability, passivity against protein absorption, antimicrobial properties, drug delivery, biocompatibility, and hemocompatibility. The demand for medical articles having these types of coatings has appreciated because they generally improve the function of the device upon implantation or insertion in the body. For example, a lubricious polymeric coating may have properties which reduce frictional forces when the device is introduced and moved within the body. Various catheter types are examples of medical articles that may be provided with hydrophilic coatings. Hydrophilic coatings are generally known in the art of implantable medical devices.

Detection of the coatings applied to an implantable medical device can be useful during the manufacturing process to detect the thickness and uniformity of the coating, as well as the completeness of coverage of the device by the coating. Many coatings applied to an implantable medical device are transparent and otherwise difficult to detect. Reagents such as colorants and dyes can be added to the coating polymer to make the coating visually detectable when applied to the device. However, these reagents can leach from the polymeric coating before, during, and after implantation.

SUMMARY

The current invention relates to hydrophilic polymeric coatings for medical devices, the coatings being visualizable in that they appear colored (e.g., blue, green, violet, red, etc.) under ambient or applied light. Since the visualizable coatings are colored, or can be induced to be colored (e.g., by fluorescence), they can be useful for a number of purposes, including assessing the quality or location of the coating during manufacture, or during a medical procedure. For example, the coating can be monitored during manufacturing or prior to use to provide information relating to coating properties such as uniformity and thickness. In some embodiments, monitoring of the coatings can be provided by an unaided human eye, a machine, or combinations thereof. For example, a coating can be visualized prior to insertion and manipulation of the medical device within the patient so the coating's location on the device is understood. The coating with the hydrophilic polymer can provide a lubricious surface which facilitates movement of the device in the body.

Generally, the coatings comprise a polymeric matrix comprising a hydrophilic polymer bonded to immobilize the polymer in the matrix, and a visualization moiety in the matrix. In some embodiments, a UV-activated photogroup is used to provide covalent bonding in the polymeric matrix. For example, in some embodiments of forming the coating, UV light can be applied to activate the photogroup to provide covalent bonding of the hydrophilic polymeric material of the coating. The covalent bonding of the hydrophilic material can provide desirable durability and lubricity of the coating on the device surface. In some instances, UV light has been reported to degrade, or photobleach visualization moieties. Surprisingly, it was found that despite UV light treatment of the coating materials, the coating maintained excellent color produced by the visualization moieties under ambient light or where the color was induced by applied light.

Embodiments of the invention include those where visualization moiety can be entrained in the coating in a particulate form, a molecular (free) form, or combinations thereof. In particulate or molecular form, covalent bonding of the visualization moiety to a coating material (e.g., hydrophilic polymer) is not required. With regards to the entrained visualization moiety, "particle-related embodiments," "molecular embodiments," and embodiments where the visualization moiety is in a mixture of particulate and molecular forms are described.

An embodiment of the present disclosure provides a medical article comprising a hydrophilic, visualizable coating comprising a polymeric matrix comprising hydrophilic polymer, the hydrophilic polymer covalently bonded to a coating material (such as another hydrophilic polymer), to a surface of the medical article, or to both. Exemplary aspects use a vinyl pyrrolidone polymer. In some embodiments, the coating further comprises a photogroup activated by UV light during the coating process. The photogroup either (a) undergoes covalent bonding to a target in the coating, or device surface, resulting in covalent immobilization of hydrophilic polymer in the coating, or (b) promotes free-radical polymerization of polymerizable material to form the hydrophilic polymer. A visualization moiety can be present in a particle or in molecular form, and the particle or molecular form can be entrained in the polymeric matrix. The visualization moiety allows for visual detection of the coating in visible light, or upon application of applied light (e.g., by fluorescence).

It was also surprisingly found that particles containing the visualization moiety were held in the coating even after soaking in water for an extended period of time. These properties can be desirable in many instances, as the colored/colorable properties can be maintained prior to and during use in the body, for example, in surgical procedures.

Other particle-related embodiments are directed to methods for forming coatings containing entrained particles comprising the visualization moiety. For example, in one particle-related method for forming the coating, a composition comprising an UV light-activatable photoreactive moiety, a hydrophilic polymer, and particles comprising a visualization moiety dispersed in the composition, can be disposed on a surface of a medical device. Upon UV irradiation, the photoreactive moiety, which can be present as a group pendent from the hydrophilic polymer, or present as one of at least two groups on a crosslinking compound, or both, undergoes active species generation with resultant covalent bonding to an adjacent chemical structure. The covalent bonding results in polymer-polymer crosslinking, bonding of the polymer to the device surface, or both. The particles comprising visualization moiety become entrained within the hydrophilic polymeric matrix.

In another particle-related method for forming the coating, the coating can be prepared comprising steps of providing a UV light-activatable photoreactive moiety, free-radically polymerizable material (such as hydrophilic monomers or macromere) capable of forming a hydrophilic polymer, and particles comprising a visualization moiety. The particles are dispersed in a composition comprising the polymerizable material, and a compound comprising a UV light-activatable photoreactive moiety can either be present in the composition, or can be pre-immobilized on a surface of the device. The composition can be disposed on a device surface and then treated with UV light. Upon treatment, the UV light-activatable photoreactive moiety initiates free-radical polymerization of the polymerizable material to cause formation of a hydrophilic polymeric matrix with entrained particles. The matrix may be formed by graft polymerization from the device surface, or by bulk polymerization. The matrix can also include polymer crosslinking.

Another embodiment of the invention is directed to a method for preparing a coating wherein the visualization moiety is entrained in the coating in molecular form. The method comprises a step of (a) providing a medical device comprising a coating, the coating comprising a polymeric matrix comprising a hydrophilic polymer comprising vinyl pyrrolidone, the polymer immobilized by bonding in the coating; and (b) contacting the coating with a composition comprising a visualization moiety comprising a stilbene chemical group and a —$SO_3R^1$ group wherein $R^1$ is independently selected from the group consisting of H, monovalent, and divalent metal cations, wherein the visualization moiety becomes entrained in the coating. In step (a) the coating can be provided "pre-formed" on the surface of a medical device, or step (a) can involve a substep(s) of forming a coating with the recited features on a surface of a medical device. It was surprisingly found that following step (b), the visualization moiety was held in the coating even after soaking in water for an extended period of time. Optionally, a UV-activated photogroup can be used to provide covalent bonding in the coating and immobilization of the vinyl pyrrolidone-containing hydrophilic polymer.

Other embodiments of the invention include those wherein the visualization moiety can be covalently bonded to a hydrophilic polymer ("covalently bonded visualization moiety embodiments"). For example, in this embodiment the invention provides a medical article comprising a hydrophilic, visualizable coating comprising a polymeric matrix comprising hydrophilic polymer, the hydrophilic polymer comprising a visualization moiety pendent from the polymer backbone. The coating also comprises a UV light-activatable photoreactive group which can result in covalent bonding of the hydrophilic polymer in the polymeric matrix. These coatings, like the particle-containing coatings, maintained excellent color, under ambient light or where the color was induced by applied light.

Some aspects of the invention further provide methods for forming coatings of the covalently-bonded visualization moiety embodiments. For example, in one method the coating can be prepared comprising steps of disposing a composition comprising a hydrophilic polymer comprising a visualization moiety pendent from the polymer backbone, and a UV light-activatable photoreactive group, on a device surface. The UV light-activatable photoreactive group can also be pendent from the hydrophilic polymer backbone, or in the coating composition as one of at least two groups on a crosslinking compound. The applied coating can then be irradiated to activate the photoreactive group that can undergo active species generation with resultant covalent bonding to an adjacent chemical structure.

In yet another method for forming the coating of the covalently-bonded visualization moiety embodiment, the coating can be prepared comprising steps of providing a compound comprising an UV light-activatable photoreactive moiety, and a free-radically polymerizable material comprising a covalently-bonded visualization moiety that can form a hydrophilic polymer. The compound comprising the UV light-activatable photoreactive moiety can either be present in the composition, or can be pre-immobilized on a surface of the device. The article surface with applied composition can be treated with UV light, and the photoreactive group acts as a polymerization initiator to free-radically polymerize the polymerizable material to cause formation of a hydrophilic polymeric matrix with visualization moiety pendent from the hydrophilic polymer.

In exemplary particle-related embodiments and covalently bonded visualization moiety embodiments, the hydrophilic polymer comprises vinyl pyrrolidone. In exemplary particle-related embodiments and covalently bonded visualization moiety embodiments the UV-activatable photoreactive group comprises a photoreactive aryl ketone. In exemplary particle-related embodiments and covalently bonded visualization moiety embodiments the coating can be present on the surface of a medical device. The medical device is exemplified by, but not limited to, cardiac and urethral catheters, and endoscopes, such as urogenital endoscopes.

Other embodiments of the invention include methods for visualizing a coating of the particle-related embodiments and covalently bonded visualization moiety embodiments. The method can include steps of inspecting the coating prior to or during insertion of the device in the body. In cases where the visualization moiety is a fluorescent compound, the method can include a step or irradiating the coating using a wavelength that results in excitation of the fluorophore, and emission of colored light from the coating. In some embodiments, the fluorescent compound is present in a coating on the surface of a device having a darker color to enable visualization of a coating otherwise difficult to detect on the darker surface if a colored dye is otherwise present in the composition.

Other embodiments of the invention include methods for treating a patient using a device comprising a coating of the particle-related embodiments or covalently-bonded visualization moiety embodiments. Exemplary treatments include those involving the vasculature or cardiac tissue, such as angioplasty, angiography, and balloon septostomy.

DETAILED DESCRIPTION

Figure 1:
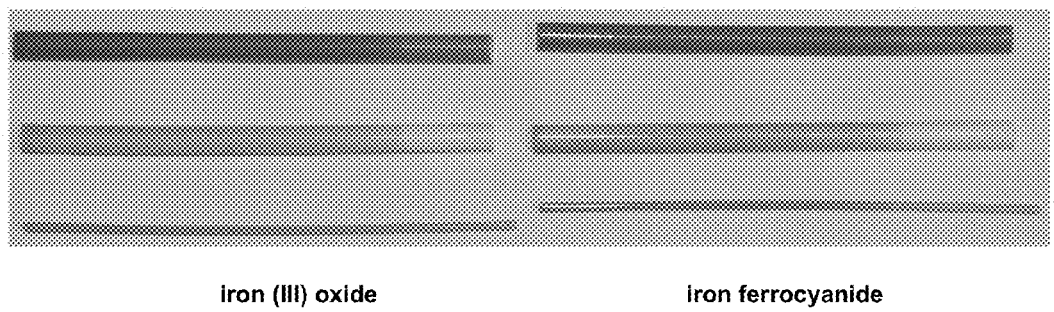
FIG. 1 shows polyether block amide rods (hereinafter PEBAX®; available from Arkema, King of Prussia, Pa.) coated with a hydrophilic photopolymer coating containing particulates of iron (III) oxide (left) or iron ferrocyanide (right), shown after UV curing of the photopolymer.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. Where any inconsistencies exist between those documents incorporated by reference and this disclosure, for example in the definition of terms, this disclosure is to govern. The publications and patents disclosed herein are provided solely for their disclosure. Nothing herein is to be construed as an admission that the inventors are not entitled to antedate any publication and/or patent, including any publication and/or patent cited herein.

Some embodiments of the present disclosure are directed to hydrophilic coatings on the surface of medical articles which can be visualized, and methods for preparing such visualized coatings. Coatings, for example, can include a hydrophilic polymeric material, a UV-activatable photogroup which can be used in forming the coatings, and a visualization moiety that can be present in the coating. As used herein, a "visualization moiety" can be a compound that provides color to the coating under ambient (visible) or applied light. The visualization moiety can be a fluorescent molecule, a colored dye, or any other suitable molecule that provides color to the coating. In some embodiments the visualization moiety can be present in the coating in particulate form. In other embodiments the visualization moiety can be present in the coating in a molecular form (e.g., where the molecules of visualization moiety are not aggregated in a particulate). In yet other embodiments the visualization moiety can be covalently attached to a hydrophilic polymer in the coating. In yet other embodiments the visualization moiety is present in the coating in two or more of the following: present in particulate form, present in molecular form, and covalently attached to a hydrophilic polymer.

The visualizable, hydrophilic coatings of the invention can be formed on a wide variety of medical devices or articles. Materials commonly used to fabricate the medical article or device include plastics (e.g., thermoplastics), metals, and ceramics. In order to describe aspects of the invention, materials that form the structure of the article (e.g., the tubing of catheter) are referred to herein as "device materials" (or "article materials") or whereas the materials used to form the polymeric coatings are herein referred to as "coating materials." Device materials are commonly referred to as biomaterial(s) as the coated article is typically placed in contact with biological fluids or tissues following implantation in the body. Any of the coating embodiments described herein, including those wherein the visualization moiety is in particulate form, or wherein the visualization moiety is covalently bonded to a hydrophilic polymer, can be associated with the surface of any device material, or any medical device as known in the art, including those exemplified herein.

Exemplary device materials on which a coating can be formed include plastic polymeric materials. Plastic polymeric materials include, but are not limited to, polyvinylchloride (PVC), polyethersulfone (PES), polysulfone (PS), polypropylene (PP), polyethylene, (PE), polyurethane (PU), polyetherimide (PEI), polycarbonate (PC), polyetheretherketone (PEEK), poly amides (nylon), and PEBAX®. Combinations of plastic polymeric materials can be used to form the device. The device may also be fabricated from one plastic polymeric material in one portion, and a different plastic polymeric material in another portion of the device. Thermoplastic polymeric materials can be formed into medical device using processes such as molding and extrusion using heat to melt the thermoplastics.

Device materials on which a coating can be formed also include metals, and metal combinations. Metals used in medical articles include, but are not limited to, platinum, gold, or tungsten, as well as other metals such as rhenium, palladium, rhodium, ruthenium, titanium, nickel, and alloys of these metals, such as stainless steel, titanium/nickel, nitinol alloys, and platinum/iridium alloys. These metals, including other alloys or combinations, can serve as suitable substrates on which a visualizable, hydrophilic coating can be formed.

Although many devices are constructed from substantially all metal materials, such as alloys, some may be constructed from both non-metal and metal materials, where at least a portion of the surface of the device can be metal. In some embodiments the metal surface can be a thin surface layer. Such surfaces can be formed by any method including sputter coating metal onto all or portions of the surface of the device.

Other surfaces that can be coated using methods of the present invention include those that include human tissue such as bone, cartilage, skin and teeth; or other organic materials such as wood, cellulose, compressed carbon, and rubber. Other contemplated biomaterials include ceramics including, but not limited to, silicon nitride, silicon carbide, zirconia, and alumina, as well as glass, silica, and sapphire. Combinations of ceramics and metals can also be coated.

Prior to coating, the device surface may be of a particular color, which may be caused by the properties of the material used to make the device, or may be caused by a colorant used in device manufacturing. The device surface prior to coating may have translucent or have a "light" color, such as white, off-white, light grey, beige, etc. Other devices surfaces, prior to coating, may have a "dark" color, such as dark grey or black. In embodiments of the invention wherein the device surface has a dark color, coatings having a visualization moiety with a fluorescence property can be useful in visualizing the coating formed on the surface.

The medical article or device can be any that can be coated and introduced temporarily or permanently into a mammal for the prophylaxis or treatment of a medical condition. These articles or medical devices include any that are introduced subcutaneously, percutaneously, or surgically to be moved or rest within an organ, tissue, or lumen of an organ.

In some aspects a visualizable hydrophilic polymeric coating can be formed on the surface of a catheter. Exemplary catheters that can be coated included, but are not limited to, guide catheters, urethral catheters, renal catheters, intravenous catheters, artificial lung catheters, blood pressure and stent graft catheters, atherectomy catheters, clot extraction catheters, percutaneous transluminal coronary angioplasty (PTCA) catheters, drug infusion catheters, angiographic catheters, neurological catheters such as neurovascular balloon catheters, thoracic cavity suction drainage catheters, electrophysiology catheters, stroke therapy catheters, abscess drainage catheters, central venous access catheters, hemodialysis catheters, and parental feeding catheters.

As an example, a visualizable hydrophilic polymeric coating can be formed on the surface of an endoscopic sheath. Endoscopic sheaths can be used in various medical procedures, including those involving the urogenital tract, the gastrointestinal tract, and the vasculature. An endoscope can be delivered through an endoscopic sheath and a visualizable hydrophilic polymeric coating on the endoscope surface that is lubricious can facilitate movement of the sheath in the body as well as the device within the sheath.

In some aspects a visualizable hydrophilic polymeric coating can be formed on the surface of a prosthetic device. Exemplary prosthetic devices include stents and grafts, such as small diameter grafts, vascular grafts, vascular stents (e.g., self-expanding stents), abdominal aortic aneurysm grafts, urological stents, and esophageal stents.

Other devices that can have a visualizable hydrophilic polymeric coating include, but are not limited to, introducers (e.g., for guide catheters), electrostimulation (e.g., defibrillator or pacer) leads, defibrillators, biosensors, coronary guidewires, peripheral guidewires, vascular and non-vascular stylets, shunts (e.g., hydrocephalus, and cerebro-spinal fluid shunts), implanted drug infusion tubes, urological implants, urinary dilators, aneurysm exclusion devices, birth control devices, endoscopic devices, blood oxygenator tubing, biliary drainage products, catheter cuffs, tympanostomy vent tubes, and drainage tubes.

In some embodiments, the visualizable hydrophilic coating can provide lubricity to the device surface so that it reduces the frictional forces associated with the movement of the device over tissue. A lubricious coating can be particularly useful for medical articles such as the catheters and endoscopic sheaths as described herein, which are moved within a lumen in the body.

Optionally, the medical device can have a "basecoat" of material between the device material (surface) and the hydrophilic coating. The basecoat can facilitate formation of a coated layer that includes the hydrophilic polymer, visualization moiety, and UV-activatable photogroup. For example, the basecoat can provide an improved material surface on which the hydrophilic polymer can spread. The basecoat can also provide material to which the UV-activatable groups can covalently bond, by providing a source of abstractable hydrogens in the basecoat material. Exemplary basecoats can be formed from Parylene (polymers based on p-xylylene) using vapor phase polymerization as known in the art, or using a silane compound such as described in U.S. Pat. No. 6,706,408.

One embodiment of the invention is directed to a visualizable polymeric coating, wherein the visualization moiety can be present in the coating in particulate form (the "particulate embodiment"). "Particulate form" refers to particles composed entirely or partially of a visualization moiety, the particles generally being small enough so that they can be entrained (e.g., held within) in the coating. Generally, the coatings of the invention are thin (e.g., such as less than 5 μm), so the particulates with visualization moiety are in the nanometer to micrometer range. The particulates containing visualization moiety can have regular or irregular shapes. In forming the coating, the particles can become entrained within the matrix of polymeric material. For example, the coating has a matrix of polymeric material, with crosslinking between the polymers in the matrix, and the particles containing the visualization moieties are physically constrained within the matrix. Optionally, the particulates can be maintained in the polymeric matrix by non-covalent forces. The particles may also be entrained in the matrix by specific covalent or non-covalent interactions between the particles and the coating polymers.

The visualization moieties in the particulates provide the coating with color, which aids in the visualization of the coating material. With some visualization moieties, such as colored dyes, the color of the coating can be observable under ambient light, including light in the visible spectrum. Using such dyes, the coating does not have to be irradiated for the user to observe the color. Using other visualization moieties, such as fluorescent compounds (fluorophores), the color of the coating can be 'induced" or enhanced by applied radiation. Such applied radiation can be within or outside the visible spectrum, depending on the absorption properties of the fluorophore. While some fluorophores require applied radiation in order for them to fluoresce and emit colored light, others may fluoresce under visible light, and their fluorescence may be enhanced by increasing the intensity of the visible light wavelength they maximally absorb.

The particulate containing the visualization moiety can be a water-insoluble pigment, such as an organic or an inorganic pigment, the pigment being the visualization moiety. During a process of forming a coating, the form of the particulate can be maintained. That is, the particles do not dissolve, or alternatively do not completely dissolve, in the solvent used to form the coating, which would otherwise cause the visualization moiety to become lost from the polymeric matrix. For example, the particulate material can be suspended in a coating composition used to form a coated layer on the device surface and after the coating process the particles of the pigment become entrained within the matrix of the coating polymer.

In some embodiments, a visualization moiety can be present in the coating as a mixture of both particulate and molecular forms. In some modes of practice, coatings having a mixture of visualization moiety in both particulate and molecular forms can be formed using a coating process where the visualization moiety has partial solubility (e.g., slight solubility) in a coating solvent. The partial solubility promotes the molecular form of the visualization moiety in the coating, and the molecular form can optionally be entrained in the coating by one or more non-covalent forces, such as hydrogen bonding and/or ionic interactions. In some embodiments the mixture can be described in terms of the amount of visualization moiety in particulate form versus in molecular form as percentage weight. For example, in a mixture, the particulate form can be greater than 50 wt %, greater than 75 wt %, greater than 90 wt %, or greater than 95 wt %.

Exemplary visualization moieties that can be present in particulate form in the coating materials include inorganic materials, such as ferrous oxide, ferric oxide, titanium oxide, zirconium oxide, Prussian Blue pigment (iron(III) ferrocyanide), and the like. Such materials can have a characteristic visible reflective optical signal, a fluorescent response to UV illumination, or both.

Other visualization moieties that can be present in particulate form in the coating materials include organic pigments, as exemplified by those listed in Table 1. These organic pigments can be substantially insoluble in aqueous compositions, partially soluble in aqueous compositions, and in some cases, exhibit some solubility in organic solvents.

TABLE 1

| Name/synonyms | Structure | CAS No. |
|---|---|---|
| Phthalo green dark/ Phalocyanine Green G/ Heliogen green/ Copper-phthalocyanine halogenated/ CI Pigment Green 7 | 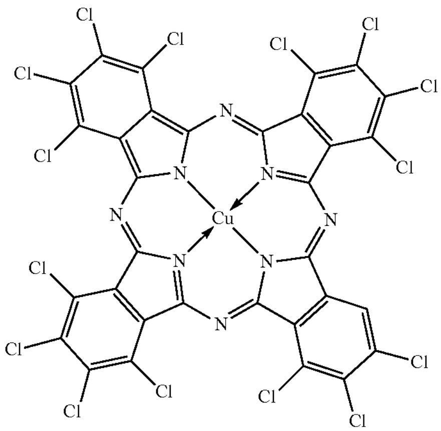 | 1328-45-6 1328-53-6 |
| Pthalo blue/ Phthalocyanine Blue BN/ Heliogen blue/ monastral blue/ Copper phthalocyanine/ C.I. 74160 | 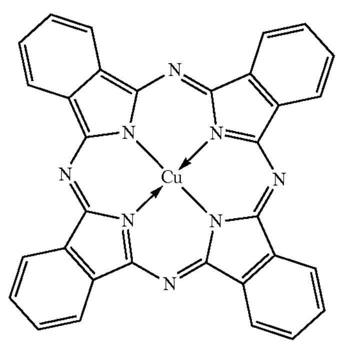 | 147-14-8 |
| Indanthren Blue/ C.I. Pigment blue 60 | 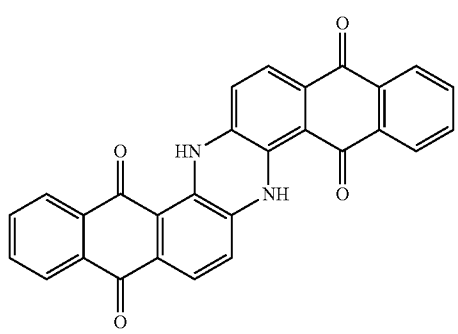 [SMILES: O=c1c2ccccc2c(=O)c2c1ccc1[nH]c3c(ccc4c(=O)c5ccccc5c(=O)c43)[nH]c12] | 81-77-6 |
| Irgazine Orange/ Pigment Orange 73/ Diketo-pyrrolo-pyrrol/ C.I. Pigment Orange 73 | 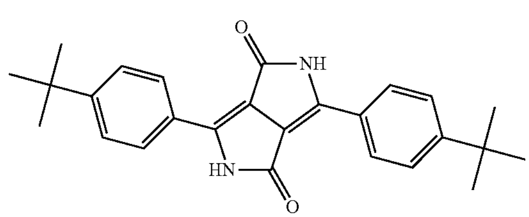 [SMILES: CC(C)(C)c1ccc(C2=C3C(=O)NC(c4ccc(C(C)(C)C)cc4)=C3C(=O)N2)cc1] | 84632-59-7 |

TABLE 1-continued

Water insoluble pigments

| Name/synonyms | Structure | CAS No. |
|---|---|---|
| Permanent Yellow Medium Pigment Yellow 154 C.I. 11781 | | 68134-22-5 |
| Dioxazine violet Dioxazine preparation C.I. Pigment Violet 37 C.I. No. 51345 | | 17741-63-8 |
| Ivory Black JU Pigment Black 9 | | 8021-99-6 |

Other particulates include visualization moieties such as organic pigments like LUMOGEN® pigments (available from BASF), which are fluorescent. Fluorescent visualization moieties are referred to herein as fluorophores, and which are exemplified in Table 3.

Exemplary LUMOGEN® pigments include perylene dyes. Further suitable dyes (C) are perylene dyes (see U.S. Pat. No. 8,349,452) of the general formula I

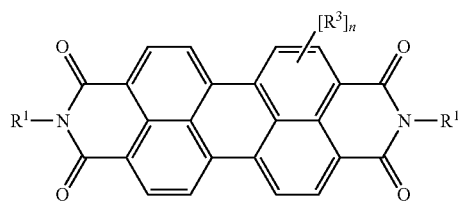

In which $R^1$ are different and preferably identical and selected from C5-C20-alkyl, straight-chain or branched, in which a carbon atom may be replaced by an oxygen atom, or phenyl, which may be substituted one or more times by C1-C13-alkyl or C1-C13-alkoxy, for example n-pentyl, isoamyl, n-hexyl, isohexyl, n-heptyl, n-octyl, n-nonyl, n-decyl, isodecyl, n-dodecyl, n-tetradecyl, n-pentadecyl, n-hexadecyl, isohexadecyl, n-octadecyl, n-eicosyl, 2-n-propoxyethyl, 2-isopropoxyethyl, 2-n-butoxyethyl, 2- or 3-ethoxy-n-propyl, 2- or 3-n-propoxy-n-propyl, 2- or 3-isopropoxy-n-propyl, 2- or 3-n-butoxy-n-propyl, 2- or 3-methoxy-n-butyl, 2- or 4-methoxybutyl, 2- or 4-ethoxybutyl, 2- or 4-(2-ethylhexyloxy)butyl, 2-, 3- or 4-methylphenyl, 2,3-dimethylphenyl, 2,4-dimethylphenyl, 2,5-dimethylphenyl, 2,6-dimethylphenyl, 2,4-diethylphenyl, 2,5-diethylphenyl, 2,6-diethylphenyl, 2,4-diisopropylphenyl, 2,5-diisopropylphenyl, 2,6-diisopropylphenyl, 2-, 3- or 4-ethylphenyl, 2,6-diethyl-4-methylphenyl, 2,6-diethyl-4-methoxyphenyl, 2,5-diethyl-4-methylphenyl, 2,5-diethyl-4-methoxyphenyl, 2-n-hexylphenyl, 2-ethyl-6-isopropylphenyl, 2-(2-methylpentyl)phenyl, 2-isopropyl-6-isobutylphenyl, 2-isopropyl-2-sec-butylphenyl, 2-ethyl-6-isobutylphenyl, 2-ethyl-6-sec-butylphenyl, 2-n-octylphenyl, 2-methoxyphenyl, 2-ethoxyphenyl, 2,3-dimethoxyphenyl, 2,3-diethoxyphenyl, 2,4-dimethoxyphenyl, 2,4-diethoxyphenyl.

In one embodiment of the present invention the radicals $R^1$ are in each case identical and selected from —$CH_2CH_2CH_2$—O—$R^2$, where $R^2$ is selected from C2-C8-alkyl.

$R^3$ are different and in particular identical and selected from hydrogen, chlorine, phenoxy or from phenoxy substituted by halogen, C1-C4-alkyl or C1-C4-alkoxy, in particular 2-, 3- or 4-fluorophenoxy, 2-, 3- or 4-chlorophenoxy, 2-, 3- or 4-bromophenoxy, 2-, 3- or 4-tert-butylphenoxy, 2-, 3- or 4-n-butylphenoxy, 2-, 3- or 4-isobutylphenoxy, 2-, 3- or 4-n-butoxyphenoxy, 2-isopropyl-4-methylphenoxy, 2,3-, 2,4-, 2,5- or 2,6-dichlorophenoxy, 2,4,5- or 2,4,6-trichlorophenoxy, 2-, 3- or 4-methylphenoxy, 2,3-, 2,4-, 2,5- or 2,6-dimethylphenoxy, 2,4,5- or 2,4,6-trimethylphenoxy, 2-methyl-4- chlorophenoxy, 2-isopropylphenoxy, 2-, 3- or 4-n- or isopropoxyphenoxy, 2,4-dimethoxyphenoxy.

Exemplary perylene dyes are according to general formula Ia

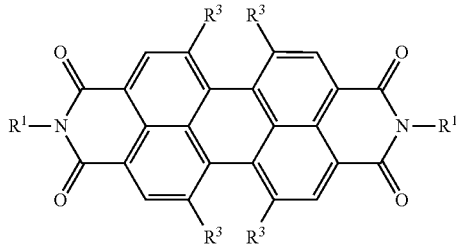

in which the variables are as defined above.

Many perylene dyes of the general formula I are commercially available under the name Lumogen® from BASF SE. Examples are Lumogen® F-Red 305 (shown below as compound b), Lumogen® F-Red 300, Lumogen® F-Yellow 083.

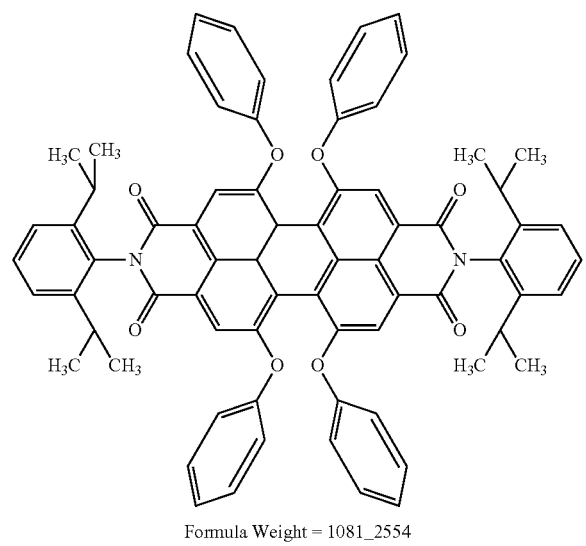

Formula Weight = 1081_2554

The visualization moiety can also be a compound known in the art as "optical brighteners" or "fluorescent brighteners" such as those listed in "Optical Brighteners," Siegrist et al. (Ullmann's Encyclopedia of Industrial Chemistry, Wiley, 2003). Optical brighteners are typically dyes that absorb light in the 340-370 nm range (ultraviolet and violet region) and re-emit light in the 420-470 nm region (blue region). The optical brightener can be used in particulate or soluble (e.g., molecular) form in the coating.

The particulate containing the visualization moiety can be any suitable material that is insoluble in, or partially soluble in the coating composition. In some embodiments, in order to provide a coating composition, a suitable solvent system can be chosen that maintains the visualization moiety in particulate form, but can dissolve the hydrophilic polymer or the monomeric material used to form the hydrophilic polymer. In yet other embodiments, the UV-activatable component can also be dissolvable in the solvent system.

In other aspects, visualization moiety solubilized in solvent or solvent system used to make the coating, which provides the visualization moiety in molecular form (non-particulate form) in the coating. An exemplary coating formulation uses a water/isopropanol mixture to solubilized the visualization moiety, along with one or more reagents that can form the polymeric material of the coating.

In order to describe aspects of the invention wherein the visualization moiety is present in the coating in particulate form, in a mixture of particulate and molecular forms, or in molecular form, the solubility of the visualization moiety can be described.

Solubility refers to the level to which a solute (e.g., the visualization moiety) dissolves in a solvent. For a visualization moiety in a particular solvent, "practically insoluble", or "insoluble" refers to having a solubility of 1 part moiety per more than 10,000 parts of solvent, "very slightly soluble" refers to having a solubility of from 1 part moiety per 1000 to 10,000 parts of solvent; "slightly soluble" refers to having a solubility of 1 part moiety per from 100 to 1000 parts of solvent; "sparingly soluble" refers to having a solubility of 1 part moiety from 30 to 100 parts of solvent; "soluble" refers to having a solubility of at least 1 part moiety per from 10 to 30 parts solvent, "freely soluble" refers to having a solubility of at least 1 part moiety per from 1 to 10 parts solvent, or "very soluble" refers to having a solubility of greater than 1 part moiety per from 1 part solvent. These descriptive terms for solubility are standard terms used in the art (see, for example, Remington: The Science and Practice of Pharmacy, $20^{th}$ ed. (2000), Lippincott Williams & Wilkins, Baltimore Md.). The solubility, or lack thereof, of a visualization moiety can be described for a visualization moiety in any desired coating solvent, such as water or an alcohol (e.g., isopropanol). Solubility of a visualization moiety can be obtained from the literature or readily determined by one of skill in the art.

The coating can be made by preparing a coating composition that includes particulates containing a visualization moiety, and material for forming the polymeric matrix of the coating. In some modes of practice, the coating composition can be made by preparing a first liquid composition that includes polymeric matrix-forming materials, and then adding a visualization moiety, such as an organic or an inorganic pigment, or a fluorescent compound, to first composition. The visualization moiety can be added to the first composition in dry form, or the visualization moiety can be dissolved or suspended in a second liquid composition, which can then be added to the first composition. In the resulting mixture (i.e., the coating composition), a substantial portion of, most of, or all of the visualization moiety can be present in particulate form.

A first composition can include polymeric matrix-forming materials such as hydrophilic polymers or hydrophilic monomers, or both, and a compound having at least one UV-activatable group that can promote polymeric matrix formation. An appropriate solvent or solvent system can be chosen so the polymeric matrix-forming materials and UV-activatable group can be dissolved. In some modes of practice the first composition uses a solvent system that includes an alcohol and water. Exemplary alcohols include short chain alcohols such as methanol, ethanol, and isopropanol. One solvent system uses a mixture of isopropanol and water. In some cases, the ratio of alcohol (e.g., isopropanol) to water can be in the range of about 10:90 to about 85:15, or about 15:85 to about 75:25, or about 25:75 to about 50:50.

The polymeric matrix-forming materials and UV-activatable group can be dissolved in the solvent system in an amount sufficient to form a desired coating layer. For example, in some compositions the total concentration of the matrix-forming materials can be in the range of from about 1% (w/v) to about 50% (w/v), or more specifically in the range about 1% (w/v) to about 5% (w/v), about 5% (w/v) to about 40% (w/v), about 1.5% (w/v) to about 15% (w/v), or about 2% (w/v) to about 10% (w/v).

The visualization moiety, when added to the first composition containing polymeric matrix-forming materials, may be in dry form, or may be dissolved or suspended in a liquid.

If the visualization moiety is dissolved in a liquid, this visualization solution, when added to the first composition containing polymeric matrix-forming materials, may cause the visualization moiety to precipitate or separate into particulates, due to it having limited or no solubility in the first composition containing polymeric matrix-forming materials. In some modes of preparation, the visualization moiety can be dissolved or suspended in an alcohol, such as methanol, ethanol, or isopropanol, at a concentration in the range of about 0.05% (w/v) to about 5% (w/v) to prepare a second composition (e.g., a "stock solution"). A desired amount of the second composition can then be added to the first composition to create the coating composition.

The particulate containing the visualization moiety can be present in a coating composition in an amount sufficient to provide a desired color and intensity of color in the formed coating. Some compounds provide a very intense color even at low concentrations in a material, and therefore some embodiments of the present disclosure contemplate use of very low amounts of visualization moiety in the coating compositions and formed coatings. For example, the concentration of the visualization moiety in particulate form can be about 1 mg/mL or greater, or 0.01 mg/mL or greater in the coating composition, with exemplary ranges of about 0.05 mg/mL to about 5 mg/mL, about 0.1 g/mL to about 0.5 mg/mL, or about 0.5 mg/mL to about 2.5 mg/mL.

Alternatively, the visualization moiety can be added in dry form directly to the first composition containing polymeric matrix-forming materials. The dry form, prior to adding to the first composition, can optionally be processed to a very fine particulate form, such as by milling or grinding. After the dry form is added, the coating composition can be treated mechanically, using processes such as vigorous stirring or shaking, or sonication to enhance the formation and dispersion of particulates in the coating composition. Sonication can be accomplished using a probe-type sonicator (e.g., from Misonix, Farmingdale, N.Y.).

Optionally, the coating composition can include a surfactant or dispersant. It has been found that the presence of a surfactant or dispersant can improve the distribution of the particulates containing visualization moiety in the coating composition, without adversely affecting the desirable coating properties such as lubricity and durability. Use of a surfactant in the coating process can advantageously provide a coating with uniform color properties. For example, an anionic surfactant, such as sodium lauryl sulfate, sodium alkyl benzene sulfonate, sodium lauroyl sarcosinate, sulfocolaurate, N-methyl-N-cocoyl taurate, sodium cocomonoglyceride sulfate, or sodium lauryl sulfoacetate can be used in the coating process. In some modes of preparing, the surfactant can be added to the first composition along with visualization agent in dry form. Vigorous stirring or shaking, or sonication, or both, can be performed after addition of the visualization agent and the surfactant. In exemplary embodiments, the concentration of the surfactant in the coating composition ranges from about 0.001% (w/v) to about 0.5% (w/v), or about 0.05% (w/v) to about 0.1% (w/v).

The visualization moiety can also be expressed in terms of the weight % of solids material in the coating composition or formed coating. For example, the weight % of the visualization moiety in particulate form can be about 0.25 weight % or greater, or 15 weight % or greater in the coating composition, with exemplary ranges of about 0.5 weight % to about 1.0 weight %, or about 1.0 weight % to about 5.0 weight %.

Generally, embodiments of the invention directed to coatings including a particulate containing the visualization moiety can be formed by a process involving UV radiation treatment of a coating composition applied to the surface of a medical device. The UV radiation treatment can affect (activate) a UV-activatable moiety in the composition so the composition undergoes free-radical polymerization of a polymerizable material to provide a hydrophilic polymeric matrix, covalent crosslinking of hydrophilic polymeric material as mediated by the UV-activatable moiety, or both. Particulates containing the visualization moiety can be present in the coating composition, or can be provided on the surface of the device, followed by the application of a coating composition to cover the particulates.

In one mode of practice, a coating composition can be prepared that includes a hydrophilic polymer, or a combination of hydrophilic polymers, a crosslinking agent comprising two or more UV-activatable photogroups, and particulates comprising visualization moiety. The composition can be disposed on a device surface and then treated with UV light to activate the photogroups of the UV crosslinking compound resulting in covalent bonding and crosslinking the hydrophilic polymers to each other to form a polymeric matrix. The polymeric matrix provides a thin coated layer on the device surface with particulates comprising visualization moiety entrained in the polymeric matrix of the coating.

Exemplary hydrophilic polymers, including hydrophilic homopolymers and copolymers, which can be synthetic or natural, that can be crosslinked with a crosslinker having UV activatable groups to form a coating are listed in the following Table 2. The hydrophilic polymer, or combination of hydrophilic polymers, can be dissolved at a concentration in the coating composition suitable for formation of a coating. The hydrophilic polymer concentration may depend on the type or types of polymers used, the solvent system, and desired coating properties (e.g., thickness). In some modes of practice, total hydrophilic polymer concentration (one or more hydrophilic polymers) in the range of about 1% (w/v) to about 50% (w/v), or more specifically in the range about 1% (w/v) to about 5% (w/v), or about 5% (w/v) to about 40% (w/v).

TABLE 2

| Hydrophilic polymers |
| --- |
| Synthetic hydrophilic polymers |
| Poly(acrylamide) (PA), poly(methacrylamide) (PMA), poly(vinylpyrrolidone) (PVP, poly(acrylic acid) (PAA), poly(ethylene glycol) (PEG), poly(vinyl alcohol) (PVA), poly(hydroxyethylmethacrylate) (PHEMA), poly(ethylene oxide), poly(ethyloxazoline), vinylpyrrolidone-methacrylamide copolymers, pyrrolidone-acrylamide copolymers, and methyl vinyl ether-maleic anhydride copolymers. |
| Natural hydrophilic polymers |
| Heparin, heparan, hyaluronic acid, chondroitin, keratan, and dermatan, alginic acid, chitosan, cellulose, chitin, collagen, dextrans, pectins, and starch. |

A hydrophilic polymer is one that can be wetted and retain water. A wetted coating can provide the surface of the coated device article with lubricity, which refers to a characterization of the frictional force associated with a coating. A coating with improved lubricity has a lower frictional force. One or more components in the coating can also provide the coated material with durability. Durability refers to the wear resistance of a polymer coating, or the ability of a coating to adhere to a device surface when subjected to forces typically encountered during use (for example, normal force, shear force, and the like). Durability of a coating can be assessed by subjecting the device to conditions that simulate use conditions. The coating can be assessed by mechanical or physical challenge, such as manipulation of the coated device by bending, twisting, or turning, and/or when the device is in contact with a portion of the body or a portion of another medical article.

In some embodiments, a crosslinking agent with two or more UV-activatable photogroups can be included in the coating composition at a concentration sufficient to provide crosslinking through covalent bonding of the hydrophilic polymers and formation of a coated layer. Exemplary amounts of the cross-linking compound present in the coating composition range from about 0.01% weight/volume (w/v) to about 5% (w/v), from about 0.1% (w/v) to about 1.0% (w/v), from about 0.01% (w/v) to about 0.08% (w/v) to about or even about 0.01% (w/v) to about 0.1% (w/v). An exemplary amount of cross-linking agent in the coating composition can be about 0.05% (w/v).

The UV activatable groups of a crosslinking compound respond to specific applied UV radiation to undergo active species generation with resultant covalent bonding to a target such as hydrophilic polymers. The crosslinking compound can also provide bonding between the hydrophilic polymer and the device surface, depending on the type of material on which the coating is formed. Some bonding may also occur between the particulate with the visualization agent and the crosslinking compound, but to the extent there is any bonding, this bonding does not affect in any substantial manner the ability of the particulate to provide visualized color to the coating.

The term "latent reactive" refers to those groups of atoms in a molecule that retain their covalent bonds unchanged under conditions of storage but which, upon activation, form covalent bonds with other molecules, such as hydrophilic polymers. Exemplary UV-activatable groups are aryl ketones, such as acetophenone, benzophenone, anthraquinone, anthrone, quinone, and anthrone-like heterocycles (for example, heterocyclic analogs of anthrone such as those having nitrogen, oxygen, or sulfur in the 10-position), or their substituted (for example, ring substituted) derivatives. Exemplary aryl ketones include heterocyclic derivatives of anthrone, including acridone, xanthone, and thioxanthone, and their ring substituted derivatives. Benzophenone, for example, can be capable of photochemical excitation with the initial formation of an excited singlet state that undergoes intersystem crossing to the triplet state. The excited triplet state can insert into carbon-hydrogen bonds by abstraction of a hydrogen atom (from a polymer or a material of a device surface, for example), thus creating a radical pair. Subsequent collapse of the radical pair leads to formation of a new carbon-carbon bond.

The UV-activatable cross-linking agent can include an ionic group and demonstrate solubility in an aqueous composition, such as a coating composition including the hydrophilic polymer. In some embodiments, the UV-activatable cross-linking agent is a compound of formula I:

$$X_1-Y-X_2 \qquad (I)$$

where Y is a radical containing at least one acidic group, basic group, or a salt of an acidic group or basic group. $X_1$ and $X_2$ are each independently a radical containing a latent photoreactive group. Spacers can also be part of $X_1$ or $X_2$ along with the latent photoreactive group, such as an aryl ketone or quinine group. Exemplary acidic groups include, for example, sulfonic acids, carboxylic acids, phosphonic acids, and the like, and suitable salts of such groups include, for example, sulfonate, carboxylate, and phosphate salts. In other embodiments of formula I, Y can be a radical that contains a basic group or a salt thereof, such as an ammonium, a phosphonium, or a sulfonium group. In some embodiments, the latent photoreactive group includes an aryl ketone or a quinone.

Exemplary crosslinking compounds of formula I include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium. Other exemplary crosslinking compounds of formula I include ethylenebis(4-benzoylbenzyldimethylammonium) salt; hexamethylenebis(4-benzoylbenzyldimethylammonium) salt; 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis(4-benzoylbenzyl)piperzinediium salt. See U.S. Pat. No. 5,714,360. The counter ion can typically be a carboxylate ion or a halide.

In some embodiments, the composition includes a crosslinking agent having formula Photo$^1$-LG-Photo$^2$, wherein Photo$^1$ and Photo$^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom. Exemplary crosslinking agents of the formula Photo$^1$-LG-Photo$^2$, are described in U.S. App. Pub. No. 2011/0245367, In some embodiments, Photo$^1$-LG-Photo$^2$ more specifically has the formula:

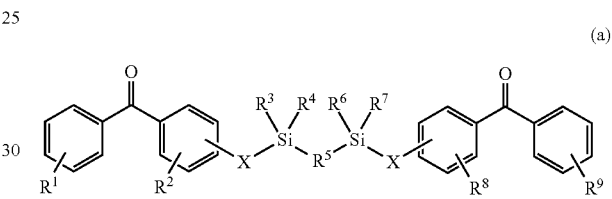

(a)

wherein $R^1$, $R^2$, $R^8$ and $R^9$ are any substitution; $R^3$, $R^4$, $R^6$ and $R^7$ are alkyl, aryl, or a combination thereof; $R^5$ is any substitution; and each X, independently, is O, N, Se, S, or alkyl, or a combination thereof;

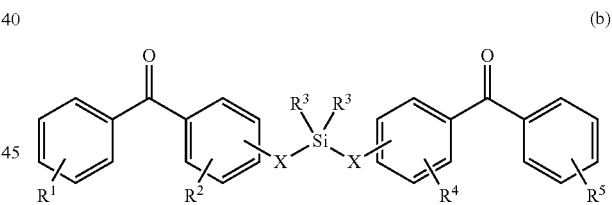

(b)

wherein $R^1$ and $R^5$ are any substitution; $R^2$ and $R^4$ can be any substitution, except OH; $R^3$ can be alkyl, aryl, or a combination thereof; and each X, independently, is O, N, Se, S, alkyl or a combination thereof;

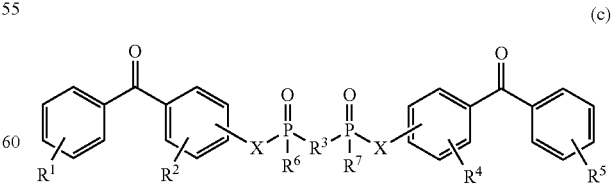

(c)

wherein $R^1$, $R^2$, $R^4$ and $R^5$ are any substitution; $R^3$ is any substitution; $R^6$ and $R^7$ are alkyl, aryl, or a combination thereof; and each X, independently, is O, N, Se, S, alkyl, or a combination thereof; or (d)

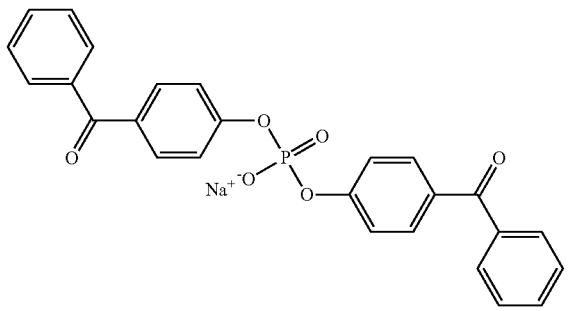

In a particular embodiment, the cross-linking agent can be bis(4-benzoylphenyl) phosphate.

In other embodiments, the composition can include an ionic photoactivatable cross-linking agent of the formula:

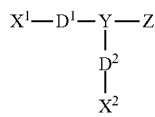

wherein $X^1$ includes a first photoreactive group; $X^2$ includes a second photoreactive group; Y includes a core molecule; Z includes at least one charged group; $D^1$ includes a first degradable linker; and $D^2$ includes a second degradable linker. Exemplary degradable ionic photoactivatable cross-linking agents are described in US Patent Application Publication US 2011/0144373 (Swan et al., "Water Soluble Degradable Crosslinker"), the disclosure of which is incorporated herein by reference.

In some aspects a non-ionic photoactivatable cross-linking agent can be used. In one embodiment, the non-ionic photoactivatable cross-linking agent has the formula $XR^1R^2R^3R^4$, where X is a non-ionic chemical backbone, and $R^1$, $R^2$, $R^3$, and $R^4$ are radicals that include a latent photoreactive group.

In other embodiments, a non-ionic photoactivatable cross-linking agent is used having the formula: $PG^2$-$LE^2$-X-$LE^1$-$PG^1$, wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Exemplary non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

In other embodiments the composition can include a non-ionic photoactivatable cross-linking agents as described in U.S. Provisional Application 61/494,724 filed Jun. 8, 2011 (now U.S. application Ser. No. 13/490,994) (Swan et al., "Photo-Vinyl Primers/Crosslinkers"), the disclosure of which is incorporated herein by reference. Exemplary cross-linking agents can include non-ionic photoactivatable cross-linking agents having the general formula R1-X—R2, wherein R1 is a radical comprising a vinyl group, X is a radical comprising from about one to about twenty carbon atoms, and R2 is a radical comprising a photoreactive group.

In other embodiments the composition can include crosslinking agents described in U.S. Publ. Pat. App. No. 2010/0274012 and U.S. Pat. No. 7,772,393 the content of all of which is herein incorporated by reference.

In other embodiments the composition can include boron-containing linking agents such as disclosed in U.S. 61/666,516, entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

(I)

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds B—$R^1$, B—$R^2$ and B—$R^3$ can be chosen independently to be interrupted by a heteroatom, such as O, N, S, or mixtures thereof.

Additional photoreactive agents, cross-linking agents, hydrophilic coatings, and associated reagents are disclosed in US 2011/0059874; US 2011/0046255; and US 2010/0198168, the content of all of which is herein incorporated by reference.

The coating composition can be applied to the surface of a medical device using any suitable technique. For example, the coating composition can be dipped, sprayed, sponged, or brushed on a device to form a layer, and then dried. In some modes of practice, the coating composition can be applied by dip-coating.

The coating process can result in the coating having a single coated layer with the coating components of the invention, or having two or more coated layers. If the coating has two or more coated layers, the coating components of the invention can be present in a single layer, or in multiple layers. If the coating has multiple coated layers, material different from the coating components of the invention can be present. Other coated layers can be optional but may be formed depending on, for example, the type of medical article coated and the intended function of the article.

The coating process can be carried out at a temperature suitable to provide a coating to the surface, or a portion of the surface, of a medical device. Generally, the coating process can be carried out at a temperature in the range of 10° C. to 50° C., or more specifically at a temperature in the range of 15° C. to 25° C. The actual coating temperature can be chosen based on aspects of the device surface to be coated, coating composition, including the coating composition solvent(s), the polymeric matrix-forming material, the particulates, and also the method used to dispose the coating composition on the device surface.

A typical dip-coating procedure involves immersing the article to be coated in the coating composition, dwelling the object in the composition for a period of time (a standard time can be generally less than about 30 seconds, and can even be less that 10 seconds in many cases), and then removing the article from the composition. After the article has been dip-coated in the coating solution, it is optionally dried. Drying can be carried out using any suitable method, including air-drying the dip-coated article. Times up to 30 minutes can be sufficient to dry the coated article although shorter times may be also sufficient. In some cases, the article does not necessarily have to be dried before being irradiated after dip-coating.

In some embodiments of the present disclosure the coating process can be carried out to provide a coating having a desired thickness that can be suitable for the device being coated and the specific application for which the coated device is intended. Exemplary thicknesses of the coating in a dried state can be in the range of about 0.2 μm to about 5 μm. In some cases, the thickness of the coating can increase upon hydration of the polymeric material in the coating. For example, the coating can swell to a thickness in the range of about 1.1 to about 3 times the thickness of the coating in the dried state. Swelling can be minimized by increasing the amount of UV-activated crosslinker in the coating composition.

Upon application of a composition to a device surface, a step of irradiating can be performed to activate the latent photoreactive groups to cause crosslinking of the hydrophilic polymers. Irradiation can be performed before and/or after the coated material dries on the surface of the device. Actinic radiation can be provided by any suitable light source that promotes activation of the photoreactive groups. Some light sources (such as those available from Dymax Corp.) provide UV irradiation in the range of about 190 nm to about 360 nm, and in some embodiments, from about 190 nm to about 290 nm. A suitable dose of radiation can be in the range of about 0.5 mW/cm$^2$ to about 2.0 mW/cm$^2$.

Unexpectedly, it was found that coatings with excellent visualization properties could be prepared without using a light filter, such as a band pass filter, during the step of UV irradiation. Therefore, aspects of the invention include irradiation processes where a filter is not used. However, optionally, a user may choose to use one or more filters, such as a band pass filter, in the methods of the invention if it is desired to provide a more specific wavelength(s) of light to the coating materials on the device surface.

In another mode of practice, the coating can be formed from by obtaining or preparing a medical device having a hydrophilic coating, and then contacting the coating with a composition that includes a visualization moiety. During the step of contacting, the visualization moiety diffuses into the coating, becomes entrained in the coating, and is difficult to remove from the coating in an aqueous solution.

The coating includes a hydrophilic polymer comprising vinyl pyrrolidone and an ultraviolet light-activated photogroup providing covalent bonding in the coating, wherein the hydrophilic polymer is covalently crosslinked to a coating material, covalently bonded to a surface of the medical article, or both. The hydrophilic polymer comprising vinyl pyrrolidone can be a vinyl pyrrolidone homopolymer or a vinyl pyrrolidone copolymer. Exemplary vinyl pyrrolidone copolymers include vinyl pyrrolidone copolymerized with one or more hydrophilic monomers, such as, but not limited to: acrylamide, methacrylamide, acrylic acid, ethylene glycol, vinyl alcohol, and hydroxyethylmethacrylate, such as vinyl pyrrolidone-methacrylamide copolymers and vinyl pyrrolidone-acrylamide copolymers. The vinyl pyrrolidone coating can, in some preparations, include a blend of two or more polymers, with at least one of the polymers in the blend being a vinyl pyrrolidone homopolymer or a vinyl pyrrolidone copolymer.

In forming the coating, the composition can include an ultraviolet light-activatable photogroup which can be activated to cause covalent bonding in the coating. For example, in one embodiment, two or more ultraviolet light-activatable photogroups can be present on a non-polymeric crosslinking compound (e.g., a compound of formula I, $X_1$—Y—$X_2$, as described herein) and present in a coating composition along with one or more vinyl pyrrolidone-containing polymer(s). In another embodiment, a polymer comprising at least one ultraviolet light-activatable photogroups pendent from the polymer backbone is present in a coating composition, and the photo-polymer comprises vinyl pyrrolidone (e.g., photo-derivatized PVP, prepared as described in U.S. Pat. No. 5,414, 075, Example 4), and/or is used with a (non-photo) vinyl pyrrolidone-containing homopolymer or copolymer.

In some modes of practice, the total hydrophilic polymer concentration (including the vinyl pyrrolidone-containing polymer) is in the range of about 1% (w/v) to about 50% (w/v), or about 5% (w/v) to about 40% (w/v). If a non-polymeric crosslinking compound is present in the coating composition, exemplary concentrations of the compound are in the range of about 0.05% (w/v) to about 5% (w/v), or about 0.1% (w/v) to about 2% (w/v). Coating composition application and UV treatment steps that can be used for forming the vinyl pyrrolidone-containing coating with UV photogroup bonding, are described herein.

After the vinyl pyrrolidone-containing coating is formed it can be contacted with a composition that includes a visualization moiety. In some aspects, the visualization moiety has one or more stilbene chemical group(s) and one or more sulfonate-containing (e.g., —SO$_3$R$^1$) group(s). In SO$_3$R$^1$, R$^1$ is independently selected from the group consisting of H, monovalent, and divalent metal cations.

In exemplary embodiments, the visualization moiety is a compound of Formula II:

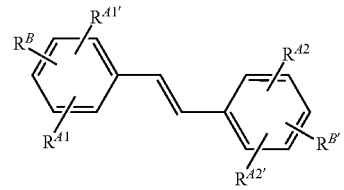

where R$^{A1}$, R$^{A1'}$, R$^{A2}$, and R$^{A2'}$ are independently selected from the group consisting of H and —SO$_3$R$^1$; and wherein R$^1$ is independently selected from the group consisting of H, monovalent, and divalent metal cations. In Formula II R$^B$ is:

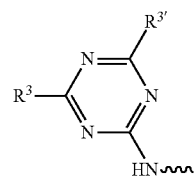

and R$^{B'}$ is

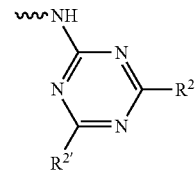

wherein R$^2$, R$^{2'}$, R$^3$ and R$^{3'}$ are

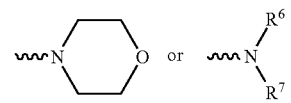

with R$^6$ and R$^7$ being independently selected from H, R$^8$R$^{10}$, phenyl, and substituted phenyl:

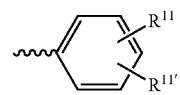

wherein $R^{11}$ and $R^{11'}$ are selected from the group consisting of H, hydrocarbyl groups, and —$SO_3R^1$, with the proviso that both $R^6$ and $R^7$ are not H; wherein $R^8$ is a — (a covalent bond) or a C1-C8 hydrocarbylene group optionally containing one or more heteroatoms; wherein $R^{10}$ is selected from the group consisting of —H, —OH, —$NH_2$, —$C(O)NH_2$, —$C(O)OR^1$ wherein $R^1$ is defined herein; or wherein, $R^{A1}$, $R^{A1'}$, $R^{A2}$, $R^{A2'}$ are as described herein, and $R^B$ and $R^{B'}$ are

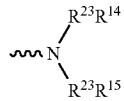

wherein $R^{14}$ and $R^{15}$ are independently selected from H, $R^8R^{10}$, phenyl, and substituted phenyl:

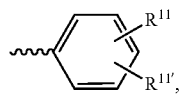

and $R^{23}$ is selected from the group consisting of a covalent bond, —C(O)—, —$CH_2NHC(O)$—, —$CH_2OC(O)O$—, —$CH_2NHC(S)NH$—, —$CH_2OC(S)NH$—, —$CH_2NHC(O)O$—, $CH_2NHC(O)NH$—, —$CH_2OC(O)$—, and —C(O)O—, as described herein.

In some embodiments, in Formula II, $R^8$ is a C1-C4 hydrocarbylene group. In some embodiments, in Formula II, $R^8$ is a C2 hydrocarbylene group. In some embodiments, in Formula II, $R^{10}$ is —OH. In some embodiments, in Formula II, $R^6$ and $R^7$ are phenyl.

In exemplary embodiments the compound of Formula II has the structure:

Other compounds of Formula II include 4,4'-bis[(4-anilino-6-hydroxy-1,3,5-triazin-2-yl)amino]stilbene-2,2'-disulfonic acid disodium salt (Blankophor™B);

Other compounds that include a stilbene chemical group(s) and/or a sulfonate-containing (e.g., —$SO_3R^1$) group(s), include 4,4'-bis(phenylureido)stilbene-2,2'-disulfonic acid disodium salt (Blankophor™R); 4,4'-di(2-sulfostyryl)biphenyl disodium salt; and 4,4'-bis(4-phenyl-1,2,3-triazol-2-yl) stilbene-2,20-disulfonic acid dipotassium salt (Blankophor™BHC).

Compositions including the visualization moiety which can be used to contact and stain the vinyl pyrrolidone-containing coating include the visualization moiety (e.g., having stilbene chemical group(s) or sulfonate-containing (e.g., —$SO_3R^1$) group(s)) at a concentration in the range of about 0.01 mg/mL to about 10 mg/mL, or more specifically about 0.1 mg/mL to about 1 mg/mL. Suitable staining solvents in which the visualization moiety is dissolved include water, alcohols, or mixtures thereof. Staining can be carried out for a very short period of time (e.g., seconds) or for longer durations (e.g., minutes); exemplary staining times range from about 10, or 30 seconds to about 2, 3, 4, or 5 minutes. The stained coatings can be rinsed in water to remove any loosely associated visualization moiety.

In another mode of practice, the coating can be formed from a coating composition that includes a hydrophilic polymer having UV-activatable photogroups that are pendent from the polymer's backbone ("hydrophilic photo-polymers"), and particulates comprising visualization moiety. The UV-activatable photogroups pendent from the polymer's backbone can provide covalent bonding to other hydrophilic polymers in the coating, or to the device surface, in a manner like the crosslinking agent does as described herein.

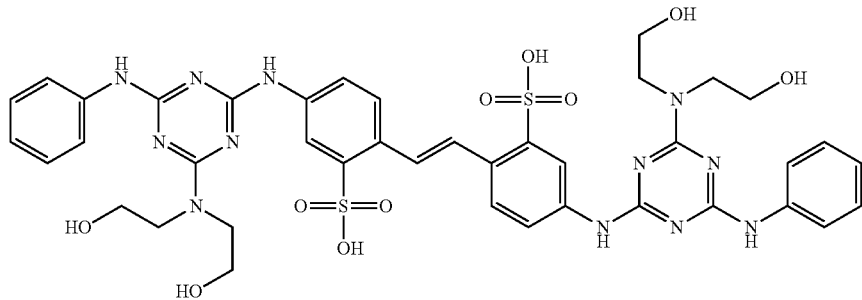 [SMILES: O=S(=O)(O)c1cc(Nc2nc(Nc3ccccc3)nc(N(CCO)CCO)n2)ccc1/C=C/c1ccc(Nc2nc(Nc3ccccc3)nc(N(CCO)CCO)n2)cc1S(=O)(=O)O]

which corresponds to Calcofluor White (fluorescent brightener 28; Table 3).

In other embodiments, the compound of Formula I has the structure:

The hydrophilic photo-polymer can have a hydrophilic backbone, such as according to any of those described in Table 2, with, for example, UV-activatable aryl ketones photogroups coupled to monomers of the backbone. Exemplary

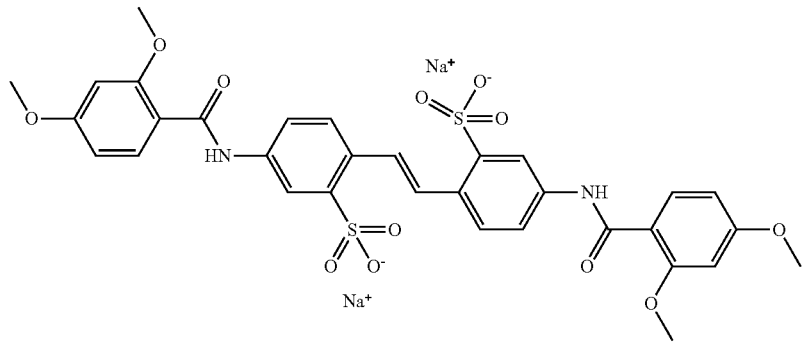

which corresponds to fluorescent brightener 34.

hydrophilic photopolymers are prepared by attaching photoreactive groups to a "preformed" hydrophilic polymer, or by copolymerizing a monomer having a photoreactive group with one or more other hydrophilic monomers. For example, a hydrophilic pre-polymer having pendent amino groups can be prepared, such as pre-polymers formed from (a) acrylamide, 2-acrylamide-2-methylpropane sulfonic acid, and N-(3-aminopropyl) methacrylamide, or (b) 1-vinyl-2-pyrrolidone and N-(3-aminopropyl) methacrylamide. The pre-polymers with pendent amino groups are derivatized with an acyl chloride (such as, for example, 4-benzoylbenzoyl chloride) under Schotten-Baumann conditions to form hydrophilic polymers with pendent aryl ketone photogroups. A photo-polyacrylamide can also be prepared by copolymerizing methacrylamide having a photoreactive group with acrylamide. The photo-methacrylamide monomer can be prepared according to the process described in U.S. Pat. No. 6,007,833 (see Examples 1 & 2), which uses the methacrylamide-oxothioxanthene monomer (N-[3-(7-methyl-9-oxothioxanthene-3-carboxamido) propyl]methacrylamide (MTA-APMA)) copolymerized with acrylamide. MTA-APMA can also be copolymerized with other types of monomers, such as vinyl pyrrolidone.

The hydrophilic photo-polymer can be used alone or with one or more other different photo-polymers, or one or more other non-photoderivitized polymer. For example, one particular composition uses a photo-PVP copolymer, a (non-photoderivitized) PVP homopolymer or copolymer, and particulates with visualization moiety. The hydrophilic polymer can be used in a coating composition alone or with one or more other photopolymer, or non-photoderivitized polymers, at a total hydrophilic polymer concentration (one or more hydrophilic polymers) in the range of about 1% (w/v) to about 50% (w/v), or more specifically in the range about 1% (w/v) to about 5% (w/v), or about 5% (w/v) to about 40% (w/v).

A coating composition including the hydrophilic photopolymer and particulates with visualization agent can be applied to the surface of a medical device using any suitable technique, such as described herein. Upon application of the composition to the surface of a medical device, irradiation of the coated surface can be performed, using any of the methods and devices as described herein.

In another mode of practice, the coating can be formed from a coating composition that includes a hydrophilic polymerizable material, a compound having UV-activatable photogroups, and particulates comprising visualization moiety. As a general matter, in this mode of forming the coating, the UV-activatable photogroups can act at least as a polymerization initiator to cause free radical polymerization of the polymerizable material, resulting in the formation of a polymer matrix in which the particles with visualization agent become entrained. Hydrophilic polymerizable material can be hydrophilic monomers or polymerizable hydrophilic polymers ("macromers"). One or more free radically polymerizable groups, for example, unsaturated carbon-carbon bonds (—C=C—) such as vinyl groups can be present on the hydrophilic polymerizable material.

Polymerization of the hydrophilic polymerizable material can be by "grafting from" polymerization from a surface, "grafting through" polymerization, or both. In grafting from polymerization, a surface bound polymerization initiator can be activated to cause polymerization and formation of the coating. In grafting through polymerization, the initiator can be dispersed among the polymerizable material.

In one graft polymerization approach, a compound having UV-activatable photogroups, such as the compound of formula I: $X_1$—Y—$X_2$, as described herein, is covalently bonded to a device surface in an initial step in the coating process. For example, a compound of formula I is disposed on a device surface having abstractable hydrogen atoms, and then irradiated so that one of the photogroups bonds to the device material, with one or more of the other photogroups maintained in, or reverting to a latent state. A coating composition including hydrophilic polymerizable material and particles with visualization agent, optionally with a crosslinking compound, is then applied to the photo-compound derivatized surface. The surface is then irradiated to activate the photogroup and drive polymerization of the polymerizable material.

Various hydrophilic monomers such as acrylic monomers, vinyl monomers, ether monomers, or combinations of any one or more of these can be used to prepare the coating. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives and/or mixtures of any of these. Vinyl monomers include, for example, vinyl acetate, vinylpyrrolidone, vinyl alcohol, and derivatives of any of these.

Hydrophilic crosslinking monomers having more than one unsaturated group can optionally be used in the coating composition. Hydrophilic crosslinking monomers include, for example, ethylene glycol dimethacrylate, diethylene glycol dimethacrylate, 2,3-propanediol dimethacrylate, 1,4-butanediol dimethacrylate, and allyl methacrylate.

Macromers include any pre-formed hydrophilic polymers, such as listed in Table 1, derivatized with one or more free-radically polymerizable group(s). Exemplary macromers can be based on one or more of the following polymers: poly(vinylpyrrolidone) (PVP), poly(ethylene oxide) (PEO), poly(ethyloxazoline), polypropylene oxide) (PPO), poly(meth)acrylamide (PAA) and poly(meth)acylic acid, poly(ethylene glycol) (PEG) (see, for example, U.S. Pat. Nos. 5,410,016, 5,626,863, 5,252,714, 5,739,208 and 5,672,662) PEG-PPO (copolymers of polyethylene glycol and polypropylene oxide), hydrophilic segmented urethanes (see, for example, U.S. Pat. Nos. 5,100,992 and 6,784,273), and polyvinyl alcohol (see, for example, U.S. Pat. Nos. 6,676,971 and 6,710,126).

In some modes of practice, the total concentration of hydrophilic polymerizable material (hydrophilic monomers, macromers, or combinations thereof) is in the range of about 1% (w/v) to about 50% (w/v), or more specifically in the range about 1% (w/v) to about 5% (w/v), or about 5% (w/v) to about 40% (w/v).

In other embodiments, the coating comprises a hydrophilic polymer with a visualization moiety, such as a fluorophore, bonded to the backbone of the polymer ("pendent" from the polymer backbone). A particulate with visualization moiety is not required in the coating, but can optionally be included if desired. The coating can also include a UV activatable group that can be used to form the coating by undergoing covalent bonding with a target moiety, promoting the polymerization of material in the composition, or both. Prior to forming the coating, the UV activatable photogroup can be present on a compound separate from the hydrophilic polymer, or can optionally be present as another group pendent from the hydrophilic compound.

Exemplary fluorophores include, for example, coumarin, coumarin-3-carboxylic acid, 7-hydroxycoumarin, 7-hydroxycoumarin-3-carboxylic acid, calcofluor white, DAPI, AMCA, Lysotracker blue, Hoechst 33258, dansyl chloride, fluorescamine, fluorescein, or rhodamine groups. More specifically, the fluorophore can comprise coumarin, coumarin-3-carboxylic acid, 7-hydroxycoumarin-3-carboxylic acid, calcofluor white, dansyl chloride, or rhodamine groups. Structures are shown in Table 3, below. Fluorophores also include optical brighteners or fluorescent brighteners as discussed herein.

TABLE 3

Exemplary fluorophores

| Name | Structure |
|---|---|
| Coumarin | 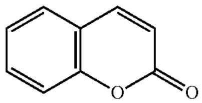 [SMILES: O=c1ccc2ccccc2o1] |
| Coumarin-3-carboxylic acid | 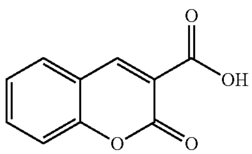 [SMILES: O=C(O)c1cc2ccccc2oc1=O] |
| 7-hydroxycoumarin-3-carboxylic acid NHS ester | 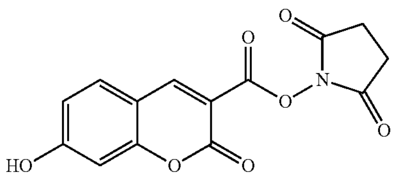 [SMILES: O=C(ON1C(=O)CCC1=O)c1cc2ccc(O)cc2oc1=O] |
| Umbelliferone (7-hydroxycoumarin) | 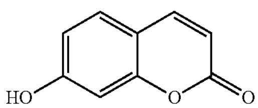 [SMILES: O=c1ccc2ccc(O)cc2o1] |
| Calcofluor White (fluorescent brightener 28) | 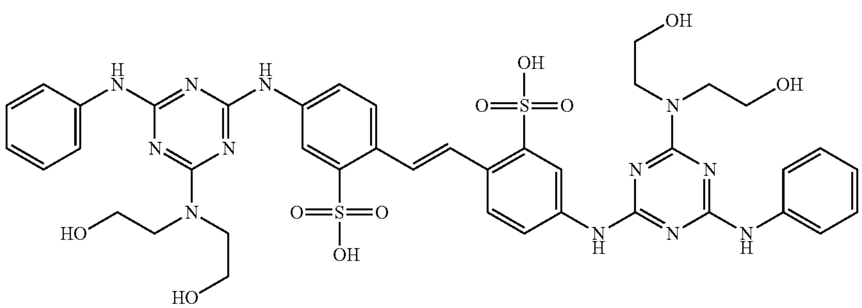 [SMILES: O=S(=O)(O)c1cc(Nc2nc(Nc3ccccc3)nc(N(CCO)CCO)n2)ccc1/C=C/c1ccc(Nc2nc(Nc3ccccc3)nc(N(CCO)CCO)n2)cc1S(=O)(=O)O] |
| DAPI (4',6-diamidino-2-phenylindole) | 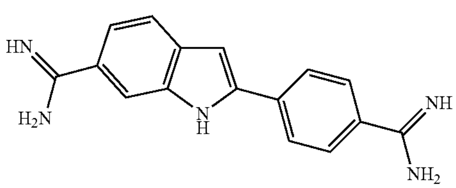 [SMILES: N=C(N)c1ccc(-c2cc3ccc(C(=N)N)cc3[nH]2)cc1] |
| AMCA (aminomethylcoumarin acetate) | |
| LysoTracker Blue | 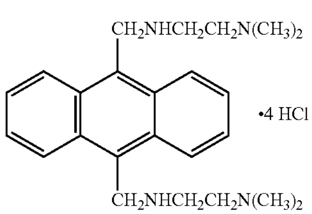 |

TABLE 3-continued

Exemplary fluorophores

| Name | Structure |
| --- | --- |
| Hoechst 33258 | 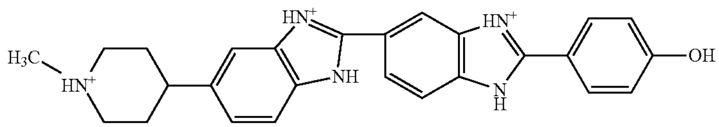 [SMILES: C[NH+]1CCC(c2ccc3[nH]c(-c4ccc5[nH]c(-c6ccc(O)cc6)[nH+]c5c4)[nH+]c3c2)CC1] |
| Dansyl chloride | 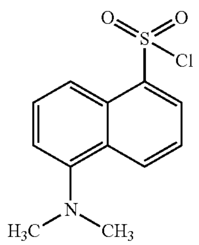 |
| Fluorescamine | 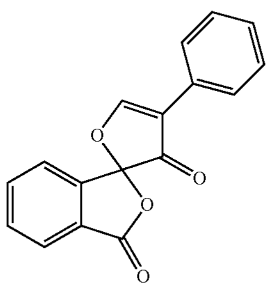 [SMILES: O=C1OC2(OC=C(c3ccccc3)C2=O)c2ccccc21] |
| Fluorescein isothiocyanate | 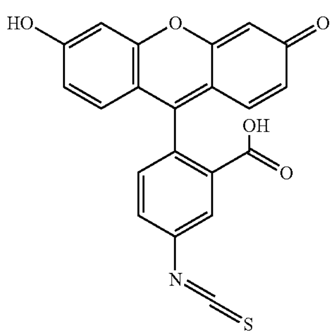 [SMILES: O=C(O)c1cc(N=C=S)ccc1-c1c2ccc(=O)cc-2oc2cc(O)ccc12] |
| Rhodamine isothiocyanate | 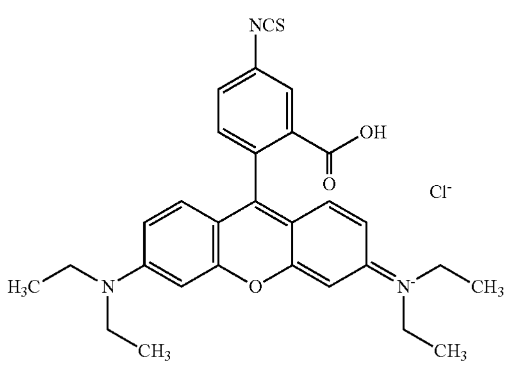 |

TABLE 3-continued

Exemplary fluorophores

| Name | Structure |
|---|---|
| Rhodamine B | (structure of Rhodamine B shown: xanthene core with two diethylamino groups, chloride counterion, and 2-carboxyphenyl substituent) |

Methods for the chemical synthesis of hydrophilic polymer derivatives formed by reacting a visualization moiety (compound) with one or more groups along the polymer backbone, or incorporating a monomer functionalized with a visualization moiety, are described. One approach involves reacting (a) a hydrophilic polymer having a pendent first reactive group with (b) a compound having a visualization moiety and second reactive group that reacts specifically with the first reactive group. The first and second reactive groups on the hydrophilic polymer and the visualization moiety-containing compound, respectively, can be chosen based on factors such as the hydrophilic polymer type, the visualization moiety, and the desired degree of loading of the visualization moiety on the polymer backbone as a result of the reaction.

For example, in some aspects the pendent visualization moiety can be present on the hydrophilic polymer in an amount in the range of 0.1% to 20% (mol), or 1% to 5% (mol), referring to the molar amount of visualization moiety to the molar amount of monomers in the hydrophilic polymer.

As a general matter, derivation of the polymer with the visualization moiety can be performed in a solvent system in which both components are soluble.

In some aspects, the pendent first reactive group can be an amine group, and the second (amine) reactive group can be selected from isothiocyanate, N-hydroxysuccinimide ester, epoxide, anhydride, aldehyde, chloroacetyl, maleimide, or mixtures thereof, and the like. An exemplary synthesis uses a synthetic hydrophilic copolymer having pendent amine groups, and an N-hydroxysuccinimide ester-derivatized visualization moiety. Other first and second reactive groups, such as (a) sulfhydryl and (b) maleimide or vinylsulfone; (a) aldehyde and (b) hydrazide; and (a) hydroxyl and (b) anhydride, respectively, are contemplated.

Exemplary synthetic hydrophilic copolymers having pendent amine groups can be prepared by a variety of processes. As a general matter, an amine containing monomer can be copolymerized with a monomer that does not have an amine group. The amount of amine-containing monomer can be controlled in copolymer synthesis to provide a hydrophilic polymer with a desired loading of visualization moiety following reaction of the amine and amine-reactive groups. For example, the copolymer can be prepared with an amount of amine-pendent monomers in the range of about 0.1% to about 20% (mol), or about 0.5% to about 5% (mol). The amount of amine-containing monomer can be chosen based on the type of visualization moiety used.

Primary amine containing monomers such as N-(2-amino-2-methylpropyl)methacrylamide (APMA), 2-aminoethyl methacrylate (AEMA), p-aminostyrene, N-(2-aminoethyl) methacrylamide, N-(3-aminopropyl) methacrylamide (APMA), allyl amine, or combinations thereof can be copolymerized with one or more monomer(s) other non-primary amine-containing monomers, such as acrylamide, methacrylamide, vinyl pyrrolidone, or derivatives thereof, to provide a hydrophilic polymer having a desired density of pendent amine groups. One exemplary copolymer is a polyvinyl pyrrolidone-N-(3-aminopropyl) methacrylamide (APMA) copolymer (PVP-APMA copolymer) wherein VP is from about 90% to about 99% (mol), and APMA is from about 1% to about 10% (mol).

The pendent primary amine groups of the copolymer can then be reacted with isothiocyanate groups of the compound containing the visualization moiety under neutral to moderately basic conditions, resulting pendent visualization moieties linked to the hydrophilic polymer backbone via thiourea groups. Alternatively, pendent primary amine groups of the copolymer can be reacted with NHS-ester groups of a of the compound containing the visualization moiety with under slightly acidic conditions, resulting pendent visualization moieties lined to the hydrophilic polymer backbone via amide groups.

In another method of synthesis, a hydrophilic polymer can be reacted with a visualization agent in the presence of a coupling compound. For example, chemical groups on the visualization moiety can be activated with a coupling agent, for example, 1,1'-carbonyldiimidazole (CDI) or dicyclohexylcarbodiimide (DCC), to facilitate covalent bonding of the visualization moiety to the polymer. CDI, for example, can selectively activate a carboxylic or hydroxyl group on the visualization moiety toward nucleophilic substitution, providing reactivity towards the amine-containing polymer. Reaction can be carried out under the following conditions: the visualization moiety is activated with CDI or DCC in a solvent such as DMSO, and amine-containing polymer is added. After some time, the reaction mixture is purified by dialysis to remove unreacted visualization moiety and reaction byproducts. In some modes of synthesis, the hydrophilic polymer having pendent UV-activatable photogroups, such as PVP-MTA-APMA, is reacted with a visualization agent in the presence of a coupling compound to provide a hydrophilic polymer having pendent UV-activatable photogroups and pendent visualization moieties.

In an alternative mode of synthesizing a hydrophilic polymer with pendent visualization moieties, a visualization moiety-derivatized monomer can be copolymerized with one or more other hydrophilic monomers. A visualization moiety-derivatized monomer can be obtained from a commercially source or can be synthesized. For example, various fluorophores such as fluorescein, naphthalene, (trifluoromethyl) coumarin, and anthracene are commercially available as polymerizable derivatives (e.g., in acrylated, methacrylated, diacrylated forms) from, for example, Sigma Aldrich.

Alternatively, visualization moiety-derivatized monomer can be formed by reacting a primary amine group monomer, such as APMA, with compound having a visualization moiety and an amine reactive group, like an NHS-ester group or isothiocyanate group, as found on fluorescein isothiocyanate or rhodamine isothiocyanate, as described herein. The visualization moiety-derived monomer can then be copolymerized with a hydrophilic monomer, for example, N-vinylpyrrolidone. Again, the resulting visualization moieties become covalently linked to the monomer, and eventually the hydrophilic polymer backbone, via thiourea groups.

A hydrophilic monomer such as that does not include a visualization moiety (such as N-vinylpyrrolidone) can be used as the primary monomer in the polymerizable composition, such that the ratio of monomer with the visualization moiety to the non-derivatized hydrophilic monomer is less than one, such as about 1:10, or about 1:20, respectively, or less. For example, the non-derivatized hydrophilic monomer can be used in an amount greater that any other monomer in the composition. In some aspects the non-derivatized hydrophilic monomer can be present in an amount of greater than 50% (mol), such as in the range of from about 75% to about 99% (mol), of from about 85% to about 99% (mol), or even from about of about 95% to about 99% (mol).

Optionally, a UV-activatable photogroup-containing monomer, such as MTA-APMA, can be copolymerized with the fluorophore-containing and hydrophilic monomers to provide the addition of UV-activatable photogroups pendent from the polymer backbone.

In some embodiments, a hydrophilic polymer comprising one or more pendent visualization moieties further comprises one or more pendent UV-activatable photogroups. The UV-activatable photogroups can be added by a process as described herein, for example, where the pendent amino groups are derivatized with an acyl chloride (such as, for example, 4-benzoylbenzoyl chloride) under Schotten-Baumann conditions to form hydrophilic polymers with pendent aryl ketone photogroups, as well as pendent visualization moieties, such as fluorophores.

Alternatively, a hydrophilic polymer comprising pendent visualization moieties and pendent UV-activatable photogroups can be formed by copolymerizing UV-activatable photogroup-derivatized monomer, a visualization moiety-derivatized monomer, and one or more other hydrophilic monomers. For example, a photo-methacrylamide monomer such as MTA-APMA, can be copolymerized with the fluorophore-containing and hydrophilic monomers to provide the addition of UV-activatable photogroups pendent from the polymer backbone.

In some aspects the pendent UV-activatable photogroup can be present on the hydrophilic polymer in an amount in the range of 0.3% to 8% (mol), or 1% to 4% (mol), referring to the molar amount of photogroup to the molar amount of monomers in the hydrophilic polymer.

A coating composition including the hydrophilic polymer with pendent visualization moiety can be used to form a coating of a device surface. If a hydrophilic polymer does not further include pendent UV-activatable photogroups, the composition can include a compound comprising one or more UV-activatable photogroups which can be activated to form the coating. For example, one exemplary composition includes (a) a hydrophilic polymer with pendent visualization moieties, such as a PVP polymer with pendent fluorescein or rhodamine, and (b) a compound having UV-activatable photogroups of the formula I: $X_1$—Y—$X_2$, as described herein. Another exemplary composition includes (a) a hydrophilic polymer with pendent visualization moieties, such as a PVP polymer with pendent fluorescein or rhodamine, and (b) a second hydrophilic polymer having pendent UV-activatable photogroups, such as a VP-APMA-MTA copolymer as described herein. If a hydrophilic polymer comprising pendent visualization moieties and pendent UV-activatable photogroups is used, a second compound comprising UV-activatable photogroups may not be required, but optionally can be included in the composition or coating process, if additional covalent bonding is desired.

In a coating process a composition comprising hydrophilic polymer with pendent visualization moiety, the composition further including a UV-activatable photogroup, can be disposed on a surface by dip-coating or any other method, such as described herein. The applied composition can then be UV irradiated to form a coated layer, such as using methods and equipment described herein. The activated UV photogroup provides covalent bonding between polymers in the coating, between polymers and the device surface, or both. Alternatively, a compound having of the formula I: $X_1$—Y—$X_2$ can be applied to the device surface prior to applying the hydrophilic polymer with pendent visualization moiety. After irradiation, the hydrophilic polymer can be covalently linked to the device surface via the reacted compound of formula I.

After the coating has been formed on the surface of a device (such as a catheter, for example) the coated device can optionally be sterilized prior to use. While any type of sterilization procedure can be employed, one exemplary procedure involves treatment with ethylene oxide. The coated device can be obtained and subject to a sterilization process, such as ethylene oxide sterilization, or a user can perform the steps of forming a hydrophilic coating and then also perform sterilization of the coated device.

Optionally, a bioactive agent can be included in the polymeric matrix comprising hydrophilic polymeric material, visualization moiety, and the UV-activated compound. Bioactive agent can be held within or released from the coating to provide a therapeutic action in association with the device surface, such as to prevent infection, or treat a pre-existing condition at the location of insertion or implantation.

Exemplary bioactive agents include, but are not limited to, antibiotics, anti-microbials, anti-inflammatory agents, anti-proliferative agents, immunomodulatory agents, anti-mitotics, and anesthetics. Particularly useful bioactive agents of these classes include macrolide antibiotics such as rapamycin (triene macrolide antibiotic) and rapamycin analogs; immunomodulatory agents such as ABT-578; anti-mitotics including taxoid drugs such as paclitaxel and docetaxel; anti-inflammatory agents such as dexamethasone and betamethasone; and anesthetics such as lidocaine or tetracaine.

To exemplify the benefits that the coatings of the present invention provide to medical devices, a visualizable hydrophilic polymer coating on the surfaces of a cardiac catheter is discussed.

A cardiovascular catheter is typically a long cylindrically-shaped device made of a plastic material that for insertion into the vasculature of a patent, with the distal end of the catheter advanced through the vasculature to a target location. For example, a catheter is inserted into femoral artery in the groin or the radial artery in the wrist, and advanced into the chambers of the heart or into the coronary arteries. Typically, a guidewire is used to push the catheter to a target location in the body. Prior to insertion of the catheter, during insertion of the catheter, or both, the coating, which (a) is colored under visible light, (b) can become colored upon treatment, or (c) can be treated to have a more intense color, can be inspected.

If the coating includes a visualization moiety, such as a fluorophore, that becomes colored upon treatment, or that can be treated to have a more intense color, light can be applied to the coating to cause light emission, such as fluorescence, or reflection. Any light source that provides light radiation of a wavelength capable of causing fluorescence can be used. In some modes of practice, a light source that provides narrow band wavelength emission corresponding to the absorption maximum of the fluorophore can be used.

Typical fluorophore excitation wavelengths are in the range of about 300 nm to about 700 nm or greater, and more typically between about 350 nm to about 600 nm. Exemplary light sources capable of providing irradiation in this wavelength include conventional fluorescent lamps, "black" lights, halogen lamps, fast halogen lamps, argon-ion lasers, plasma arc, LED (light emitting diode)-based sources. Light sources capable of providing light radiation in this wavelength are commercially available from, for example UVP (Upland, Calif.), Dymax (Torrington, Conn.), or EFOS, Inc. (Mississauga, Ontario, Canada).

The use of the visualization moiety enables visual assessment of coating quality, including thickness. The presence of the visualization moiety can also be useful for determining if the coating includes any undesirable features or irregularities such as coating cracks or areas of delamination. Visualization of the polymeric material can be enhanced by reducing or eliminating the amount of background light.

A catheter with a visualizable hydrophilic polymer coating can be used for cardiac catheterization. Cardiac catheterization includes procedures such as coronary angiography, as well as left ventricle angiography. Once the catheter is in place, it can be used to perform any one of a number of procedures including angioplasty, angiography, and balloon septostomy. The visualizable hydrophilic polymer-coated catheter can be used in various analytic procedures, such as measuring blood pressure within the heart, blood oxygenation, and the contractile patterns and strength of cardiac muscle. The catheter can also be used in procedures to inject dye into the coronary arteries, such as coronary angiography or coronary arteriography. In this process, a catheter having the visualizable hydrophilic polymer coating can be inserted using a guidewire and advanced towards the heart to a position above the aortic valve. The guidewire can then be removed. The catheter can then be engaged with the origin of the coronary artery (either left main stem or right coronary artery) and x-ray opaque iodine-based contrast can be injected to make the coronary vessels show up on the x-ray fluoroscopy image. A visualizable hydrophilic polymer-coated catheter can also be used in balloon-based procedures such as coronary angioplasty (e.g., percutaneous coronary intervention; PCI).

As another example, a visualizable hydrophilic polymer coating can be formed on the surface of an endoscopic sheath. Endoscopic sheaths can be used in various medical procedures, including those involving the urogenital tract, the gastrointestinal tract, and the vasculature. For example an endoscope can be delivered through an endoscopic sheath. A visualizable hydrophilic polymer coating that is lubricious can facilitate movement of the sheath in the body as well as the device within the sheath.

Example 1

Use of Visible Inorganic Pigments to Visualize Polymer Coatings

Coating solutions of polyvinylpyrrolidone (PVP) (15 mg/mL Kollidon K90®, 15 mg/mL Kollidon K30®), photo-derivatized PVP (15 mg/mL; prepared as described in U.S. Pat. No. 5,414,075, Example 4), and a photocrosslinker (1.5 mg/mL; 4,5-bis(4-benzoylphenylmethyleneoxy)benzene-1, 3-disulfonic acid, prepared as described in U.S. Pat. No. 6,278,018) were prepared in a mixture of water and isopropyl alcohol (IPA; ratio of water/IPA=60/40). A visible inorganic pigment (Table 4) was mixed in the dry state into the coating solution to yield 0.5 mg/mL (bringing total solids to ~47 mg/mL). The pigments settled to the bottom of the solution. The addition of a surfactant (sodium lauryl sulfate, ~0.5% final concentration) to the solution followed by shaking and sonication in a bath sonicator for about 10 minutes led to stable suspensions of the iron and titanium pigments. Iron ferrocyanide partially dissolved upon addition of the surfactant.

TABLE 4

| Inorganic visible pigments | | |
|---|---|---|
| Pigment | Supplier | Part No. |
| Iron (III) oxide | Aldrich | 544884 |
| Iron ferrocyanide | Sigma | 234125 |

PEBAX® rods were wiped with IPA and then dipped into the coating solution and slowly removed to produce a thin coating on the substrate. The coating was dried at ambient temperature and pressure and then cured in a UV chamber for 3 minutes, at approximately 8 inches from the UV bulb using a DYMAX™ Cure System (light system commercially available from Dymax; Torrington, Conn., wavelength range 330-340 nm).

Coatings without pigments are not visible to the eye. Coatings prepared with iron ferrocyanide or iron (III) oxide pigments were visible to the unaided eye after coating and curing (FIG. 1). The UV curing process did not alter the appearance of the pigments in the coating.

Example 2

Use of Water-Insoluble Visible Organic Pigments to Visualize Polymer Coatings

Coating solutions of PVP, photo-derivatized PVP, and a photocrosslinker were prepared at 46.5 mg/mL total solids in a mixture of water and IPA (as described in Example 1). Water-insoluble powdered pigments (Table 5) were dissolved or suspended in IPA at 10 mg/mL and added to the coating solution to yield a concentration in coating solution of 0.5 mg/mL (bringing total solids to ~47 mg/mL, neglecting dilution caused by addition of the pigment stock). The visible pigments formed stable solutions/suspensions when diluted from IPA stock into coating solutions. All pigments exhibited at least some suspended precipitate and some appearance of dissolution in the coating solutions.

TABLE 5

| Organic visible pigments | | |
|---|---|---|
| Pigment | Supplier | Part No. |
| Heliogen green | Kremer Pigments | 23000 |
| Heliogen blue | Kremer Pigments | 23050 |
| Indanthren blue | Kremer Pigments | 23100 |
| Irgazine orange | Kremer Pigments | 23178 |
| Permanent yellow medium | Kremer Pigments | 23310 |
| Dioxazine violet | Kremer Pigments | 23451 |

PEBAX® rods were wiped with IPA and then coated as described in Example 1.

Figure 2:
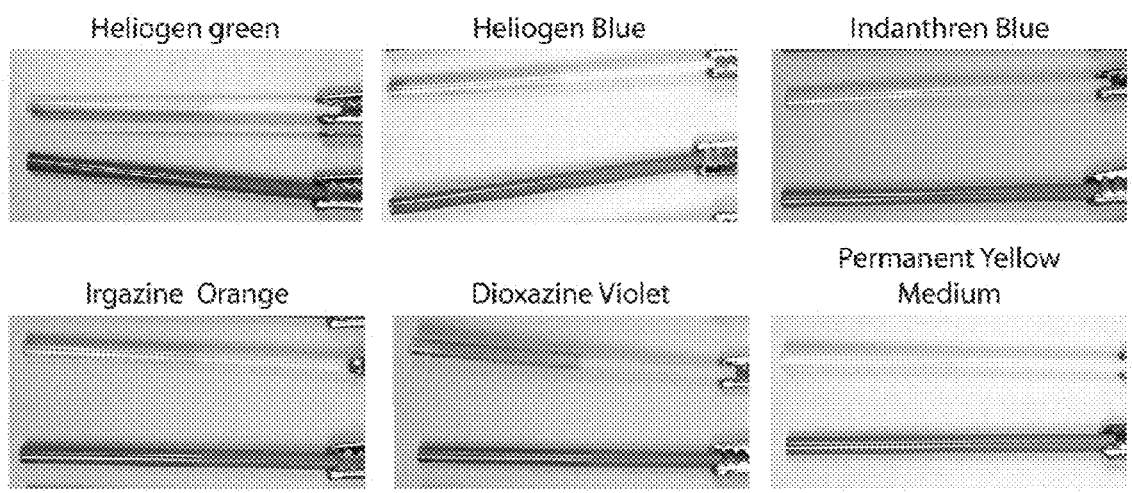
FIG. 2 shows PEBAX® rods coated with a hydrophilic photopolymer coating containing various organic pigments, shown after UV curing of the photopolymer.

The visible pigments made the otherwise invisible coatings visible by eye (FIG. 2). The UV curing process did not alter the appearance of the pigments in the coatings.

The coated part was then placed in water at room temperature for 2 h. The coatings remained visible after soaking. Evaluation of the soak solution with UV-visible spectroscopy indicated no measureable pigment leached out of the coating and into the water.

Example 3

Use of Water-Insoluble Fluorescent Pigments to Visualize Polymer Coatings

Coating solutions of PVP, photo-derivatized PVP, and a photocrosslinker were prepared at 46.5 mg/mL total solids in a mixture of water and IPA (as described in Example 1). Water-insoluble fluorescent powdered pigments (Table 6) were dissolved or suspended in IPA at 10 mg/mL and added to the coating solution to yield a concentration in coating solution of 0.5 mg/mL (bringing total solids to ~47 mg/mL). The fluorescent pigments formed stable solutions/suspensions when diluted from IPA stock into coating solutions.

TABLE 6

Water-insoluble fluorescent pigments

| Fluorescent pigment | Supplier | Part No. |
|---|---|---|
| Lumogen ® Perylene - fluorescent red | Kremer Pigments | 94720 |
| Lumogen ® Perylene - fluorescent pink | Kremer Pigments | 94739 |
| Lumogen ® Perylene - fluorescent orange | Kremer Pigments | 94738 |
| Lumogen ® Perylene - fluorescent yellow | Kremer Pigments | 94700 |
| Lumogen ® Perylene - fluorescent green | Kremer Pigments | 94737 |
| Lumogen ® dye, naphthalimide derivative | Kremer Pigments | 94736 |
| Lumogen ® Naphthalimide, fluorescent brightener 331 | Kremer Pigments | 94730 |

PEBAX® rods cleaned and coated as described in Example 1.

Figure 3:
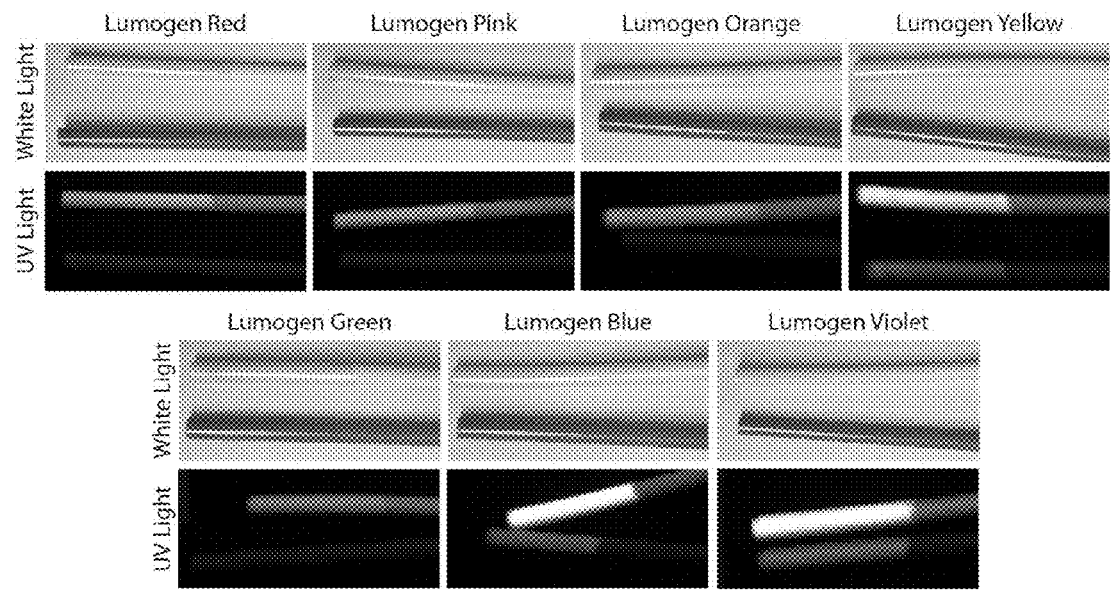
FIG. 3 shows PEBAX® rods coated with a hydrophilic coating containing water-insoluble fluorescent pigments, shown after UV curing of the photopolymer.

Some of the fluorescent pigments were sufficiently colored that they made the otherwise invisible coatings visible by eye when viewed in white light (FIG. 3). Others made the coatings visible only when illuminated by UV light (366 nm), which caused the pigments to fluoresce (FIG. 3). Surprisingly, the UV curing process neither altered the appearance of the fluorescent pigments when viewed under white light nor affected the fluorescence of the pigments when viewed under UV light.

The coated part was then placed in water at room temperature for 2 h. The coatings remained visible/fluorescent after soaking. Evaluation of the soak solution with fluorescence spectroscopy indicated no measureable fluorescent pigment leached out of the coating and into the water.

Example 4

Use of Water-Insoluble Fluorescent Dyes to Visualize Polymer Coatings

Coating solutions of PVP (Kollidon K90®, 5 mg/mL), photo-derivatized PVP (13 mg/mL), and a photocrosslinker (0.2 mg/mL); were prepared in a mixture of water and IPA (25/75 water/IPA). Water-insoluble fluorescent powdered dyes (Table 7) were dissolved or suspended in IPA at 10 mg/mL. Dansyl chloride and coumarin formed clear solutions in IPA. Coumarin-3-carboxylic acid partially dissolved; some suspended particles remained. The stock fluorescent dye solution was added to the coating solution to yield a concentration of fluorescent dye in coating solution of 0.5 mg/mL (bringing total solids to ~18.7 mg/mL).

TABLE 7

Water-insoluble fluorescent dyes

| Fluorescent dye | Supplier | Part No. |
|---|---|---|
| Dansyl chloride | Sigma | D2625 |
| Coumarin | Sigma | C4261 |
| Coumarin-3-carboxylic acid | Aldrich | C85603 |

Pebax rods were cleaned and coated as described in Example 1.

Figure 4:
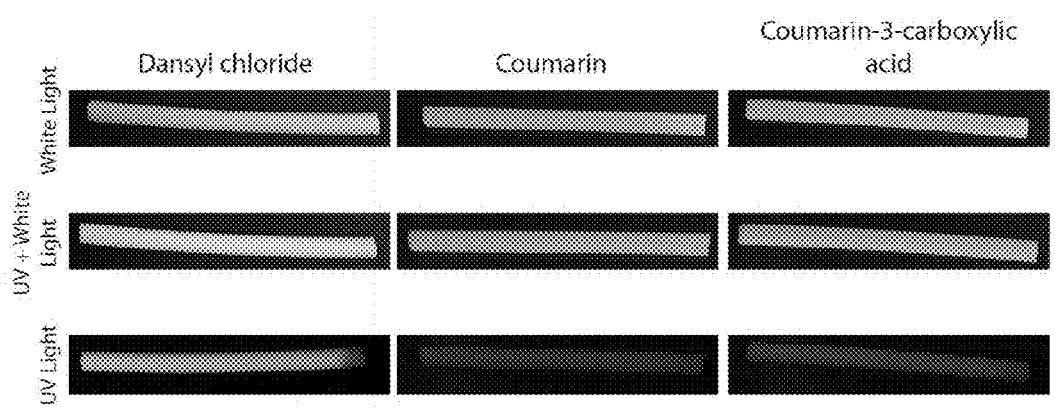
FIG. 4 shows PEBAX® rods coated with a hydrophilic photopolymer coating containing water-insoluble fluorescent dyes, shown after UV curing of the photopolymer.

None of the coatings were visible to the unaided eye (FIG. 4). Dansyl chloride made the coatings visible when illuminated by UV light (366 nm), which caused the dye to fluoresce (FIG. 4). Surprisingly, the UV curing process did not affect the fluorescence of the dye when viewed under UV light. Neither of the two coumarin derivatives enabled visualization of the coatings.

Example 5

Use of Water-Soluble Fluorescent Dyes to Visualize Polymer Coatings

Coating solutions of PVP, photo-derivatized PVP, and a photocrosslinker were prepared at 18.2 mg/mL total solids in a mixture of water and IPA (as described in Example 4). Several water-soluble fluorescent dyes (Table 8) were dissolved in water at 10 mg/mL and added to the coating solution to yield a concentration in coating solution of 0.5 mg/mL (bringing total solids to ~18.7 mg/mL). The fluorescent dyes formed stable solutions when diluted from water stock into coating solutions.

TABLE 8

Water-soluble fluorescent dyes

| Fluorescent dye | Supplier | Part No. |
|---|---|---|
| Rhodamine B | Sigma | R6626 |
| Fluorescent Brightener 28 | Sigma | F3543 |

Pebax rods were cleaned and coated as described in Example 1.

Figure 5:
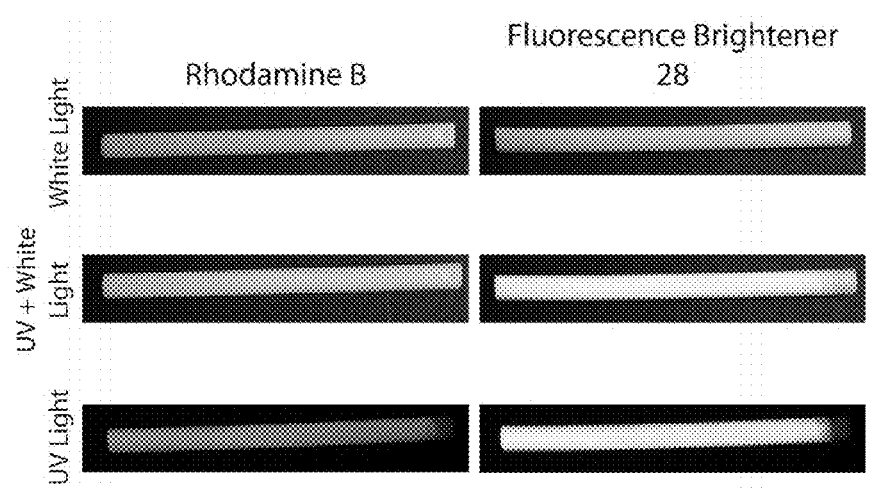
FIG. 5 shows PEBAX® rods coated with a hydrophilic photopolymer coating containing water-soluble fluorescent dyes, shown after UV curing of the photopolymer.

Rhodamine B was sufficiently colored that it made the otherwise invisible coatings visible by eye when viewed in white light (FIG. 5). Fluorescent brightener 28 made the coatings visible only when illuminated by UV light (366 nm), which caused the pigments to fluoresce (FIG. 5). Surprisingly, the UV curing process neither altered the appearance of the fluorescent pigments when viewed under white light nor affected the fluorescence of the pigments when viewed under UV light.

The coated parts were then placed in PBS, pH 7.4 at room temperature for 1 d. Surprisingly, the coatings remained visible (rhodamine B) and/or fluorescent (rhodamine B and fluorescent brightener 28) after soaking. Evaluation of the soak solution with fluorescence spectroscopy indicated that a small amount (<10%) of the fluorescent pigment leached out of the coating and into the water.

Control samples having coatings prepared in the same manner but that were not crosslinked with UV were subjected to the same analysis. These coatings were visible to the same extent when viewed under UV light. However, the coating dissolved completely within three hours when placed in PBS, pH 7.4 at room temperature. The amount of fluorescent dye present in the soak solution was more than ten-fold that measured in samples with crosslinked coatings.

Example 6

Synthesis of PVP-Rhodamine Polymer

Water (40 mL) was added to a 100 mL amber bottle containing PVP-APMA (1 g). The polymer was allowed to dissolve for about 15 min at room temperature. At which point, $NaHCO_3$ (0.05 g) was added. After 5 min the heterogeneous mixture of rhodamine β isothiocyanate (0.18 g) in 5 mL of water was added. The reaction mixture was allowed to stir for additional 2 h at room temperature. The crude product was purified by dialysis against water. After lyophilization 1 g of PVP-rhodamine was collected as a purple solid.

Example 7

Synthesis of PVP-Fluorescein Polymer

The procedure described in Example 6 was repeated substituting rhodamine isothiocyanate with fluorescein isothiocyanate (0.13 g). The final product, PVP-fluorescein (0.87 g), was collected as a yellow solid.

Example 8

Synthesis of PVP-Rhodamine-BBA Polymer

Rhodamine B (0.25 g) was placed into a dry 100 mL round-bottom flask which was under nitrogen and equipped with a stir bar. After DMSO (anhydrous, 50 mL) was added, the solution was dark red. The solution cleared and became less colored after the addition of TEA (0.15 mL). After 30 min of stirring at room temperature, CDI (0.09 g) was added to the reaction mixture and it was allowed to stir for additional 30 min. PVP-APMA-BBA (2 g) was dissolved in a separate 100 mL flask in DMSO (40 mL) and was added to the activated rhodamine at once. After 16 h, the reaction mixture was poured into 100 mL of water and dialyzed (water, 12-14 kDa). Lyophilization gave 1.6 g of a pale pink solid.

Example 9

Synthesis of PVP-Fluorescent Brightener 28-BBA Polymer

The procedure described in Example 8 was repeated substituting fluorescent brightener 28 (0.48 g) for rhodamine B. The final product, PVP-fluorescent brightener 28-BBA (2.04 g) was collected as a white solid.

Example 10

Synthesis of PVP-Dansyl-BBA Polymer

The procedure described in the Example 8 was repeated substituting dansyl chloride (0.17 g) for rhodamine B. The final product, PVP-dansyl-BBA (1.7 g) was collected.

Example 11

Synthesis of PVP-Hydroxycoumarin-BBA Polymer

PVP-APMA-BBA (2 g) was dissolved in anhydrous DMSO (50 mL) in a dry 100 mL round-bottom flask which was under nitrogen and equipped with a stir bar. TEA (0.15 mL) was added to the reaction mixture followed by 7-hydroxy coumarin-3-carboxylic acid-N-succinimidyl ester (25 mg). After 16 h, the reaction mixture was poured into 50 mL of water and dialyzed (water, 12-14 kDa). Lyophilization gave 1.8 g of a pale green solid.

Example 12

Preparation of PVP-Fluorescent Brightener 28 Adduct

PVP (Kollidon K90®, BASF) (100 mg) and fluorescent brightener 28 (10 mg) were dissolved in water (5 mL). The solution was placed in a 12-14 kDa dialysis tube. The mixture was dialyzed for 7 days against water to remove unbound fluorescent brightener. The resulting PVP-fluorescent brightener adduct was soluble in water and fluoresced when viewed under UV light.

Example 13

Use of PVP Polymers with Pendant Fluorescent Groups to Visualize Polymer Coatings Coating solutions of PVP (Kollidon K90®, 13 mg/mL), photo-derivatized PVP (5 mg/mL), a photocrosslinker (0.2 mg/mL), and one of the polymers from Examples 8-11 (5 mg/mL) were prepared in a mixture of water and IPA (25/75 water/IPA). The fluorescently-labeled polymers dissolved completely in the coating solutions.

Pebax rods were cleaned and coated as described in Example 1.

Figure 6:
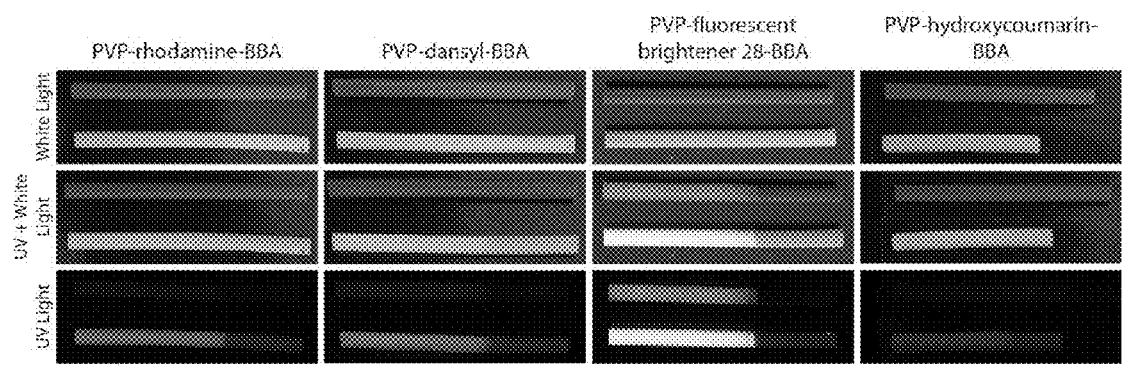
FIG. 6 shows PEBAX® rods coated with a hydrophilic photopolymer coating containing the fluorescently-labeled PVP, shown after UV curing of the photopolymer.

Coatings containing PVP-rhodamine B made the otherwise invisible coatings visible by eye when viewed in white light (FIG. 6). None of the other PVP-fluorophore coatings were visible in white light. All of the PVP-fluorophore coatings were visible when illuminated by UV light (366 nm), which caused the pendant fluorophores to fluoresce (FIG. 6). Surprisingly, the UV curing process neither altered the appearance of the fluorescently-modified polymers when viewed under white light nor affected the fluorescence of the fluorescently-modified polymers when viewed under UV light.

Example 14

Fluorescent Brightener Staining of PVP Coatings

A first coating solution of PVP (Kollidon® 90, 5 mg/mL), photo-derivatized PVP (13 mg/mL), and a photocrosslinker (0.2 mg/mL; Example 1) was prepared in a mixture of water and IPA (25/75 water/IPA) was prepared as described in Example 4. A second coating solution having the same concentrations of PVP and crosslinker reagents, but additionally including fluorescent brightener 28 (FB28; at 0.5 mg/mL) in the coating solution, was prepared. A third coating solution of photo-polyacrylamide (15 mg/mL in 15/85 water/IPA; see U.S. Pat. No. 6,007,833, Examples 1 & 2) was prepared.

Individual polystyrene (PS) rods were separately coated with the first non-fluorescent coating solution (PVP), the second fluorescent coating solution (PVP (+) FB28), and the third non-fluorescent coating solution (PA) using a dipcoating procedure, followed by UV treatment, as described in Example 1.

The non-fluorescent (PVP and PA)-coated PS rods were then placed in an aqueous solution of FB28 (5 mg/mL) for 30 seconds at approximately 20° C., removed, and then rinsed and rubbed under flowing water for 30 seconds. The PVP-coated PS rods with FB28 added during the coating step, and PVP- and PA-coated PS rods stained with FB28 following the coating step, were subsequently visualized by illuminating the rods with UV light (366 nm). The PVP-coated PS rods stained with FB28 showed brighter fluorescence than the PVP-coated PS rods where FB28 was present in the coating solution, indicating staining of PVP by the FB28 solution. The PA-coated PS rods stained with FB28 did not show fluorescence following rinsing with water, indicating that FB28 did not stain the polyacrylamide-based coating.

To test the possible extraction of FB28 from the PVP coating, the FB28-stained PS rods were soaked in water at approximately 20° C. for periods up to six days. Soaking in water for up to six days led to only a slight decrease in fluorescence of the coating. Soaking coated parts for 20 h in aqueous urea (6 M), which should interfere with hydrogen bonding between FB28 and PVP, led to a greater, but not complete, extraction of FB28 from the coating.

Example 15

Fluorescent Brightener Staining of PVP Coatings on Dark Substrates

A coating solution of a photo-derivatized PVP (10 mg/mL), photo-derivatized polyacrylamide (10 mg/mL), PVP (Kollidon® 90; 20 mg/mL), and a photocrosslinker (0.2 mg/mL) was prepared in a mixture of IPA and water (15/85). Samples made of Nylon 12 that were black in color were coated with the coating solution using a dipcoating procedure, followed by UV treatment, as described in Example 1. Samples were placed for 5 minutes in a solution of Congo Red (0.35% in water, approx. 20° C.), which is commonly used to visualize PVP-containing coatings. Excess staining solution was rinsed with water and the samples were inspected. The expected red stain of the coating was not visible due to the dark color of the substrate; this prevented inspection of the coating. A second part, coated by the same process, was placed in an aqueous solution of FB28 (1 mg/mL) for 60 seconds at approx. 20° C., removed, and rinsed with water. The sample was then viewed under illumination with 366 nm light. The coating on the black substrate fluoresced and was able to be easily inspected.

What is claimed is:

1. A medical device having a coating, the coating a polymeric matrix comprising
    a hydrophilic polymer, an ultraviolet light-activated aryl ketone photogroup providing covalent bonding in the coating and covalently bonded to the hydrophilic polymer, and a visualization moiety pendent from the hydrophilic polymer,
    wherein the hydrophilic polymer is covalently crosslinked to other hydrophilic polymers, covalently crosslinked to a coating material that is different than the hydrophilic polymer, covalently bonded to a surface of the medical article, or combinations thereof, and
    wherein the visualization moiety comprises a fluorophore that provides color under visible light, or can be induced to provide color.

2. The device of claim 1 wherein the fluorophore comprises coumarin, coumarin-3-carboxylic acid, 7-hydroxycoumarin, 7-hydroxycoumarin-3-carboxylic acid, calcofluor white (fluorescent brightener 28), DAPI, AMCA, Lysotracker blue, Hoechst 33258, dansyl chloride, fluorescamine, fluorescein, or rhodamine.

3. The device of claim 1 wherein the visualization moiety is made pendent from the hydrophilic polymer by reacting an amine group on the hydrophilic polymer with an amine-reactive group on the visualization moiety.

4. The device of claim 1 wherein the ultraviolet light-activated aryl ketone photogroup is pendent from the hydrophilic polymer.

5. The medical device of claim 4, wherein the hydrophilic polymer is formed by a process comprising polymerizing a monomer composition comprising an UV-activatable aryl ketone photogroup-derivatized monomer.

6. The device of claim 1 wherein the hydrophilic polymer comprises vinylpyrrolidone.

7. The device of claim 1 wherein the hydrophilic polymer comprises aminopropylmethacrylamide (APMA).

8. The device of claim 1 wherein the UV light-activatable aryl ketone photogroup is present on a compound of formula I:

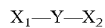

where Y is a radical containing at least one acidic group, basic group, or a salt of an acidic group or basic group, and $X_1$ and $X_2$ are each independently the UV light-activatable aryl ketone photogroup.

9. The device of claim 1 which is a cardiovascular catheter or an endoscopic sheath.

10. The medical device of claim 1, wherein the hydrophilic polymer is covalently crosslinked to a coating material that is different than the hydrophilic polymer, wherein the coating material that is different than the hydrophilic polymer is a basecoat.

11. The medical device of claim 1, wherein the hydrophilic polymer is covalently crosslinked to a coating material that is different than the hydrophilic polymer, wherein the coating material that is different than the hydrophilic polymer is a homopolymer or copolymer that does not have a pendent UV-activatable aryl ketone photogroup.

12. A method for forming the coating of claim 1 comprising steps of
    (a) providing a composition comprising a hydrophilic polymer comprising a pendent visualization moiety, wherein the visualization moiety comprises a fluorophore that provides color under visible light, or can be induced to provide color;
    (b) providing a UV light-activatable aryl ketone photoreactive moiety that is present in the composition, pre-immobilized on a surface of a device, or pendent from the hydrophilic polymer;
    (c) disposing the composition on a surface of a device; and
    (d) treating the composition on a surface of a device to cause formation of a hydrophilic polymeric of the coating wherein the aryl ketone photoreactive moiety is covalently bonded to the hydrophilic polymer in the coating.

* * * * *

UNITED STATES PATENT AND TRADEMARK OFFICE
CERTIFICATE OF CORRECTION

| | | |
|---|---|---|
| PATENT NO. | : 8,956,682 B2 | Page 1 of 1 |
| APPLICATION NO. | : 13/855260 | |
| DATED | : February 17, 2015 | |
| INVENTOR(S) | : Nathan A. Lockwood, Bruce M. Jelle and Aleksey V. Kurdyumov | |

It is certified that error appears in the above-identified patent and that said Letters Patent is hereby corrected as shown below:

In the claims

Column 41,
Line 20, Claim 1, "crosslinked to other" should be -- crosslinked via the aryl ketone photogroup to other --

Column 41,
Line 21, Claim 1, "crosslinked to a coating" should be -- crosslinked via the aryl ketone photogroup to a coating --

Column 41,
Line 23, Claim 1, "bonded to a surface" should be -- bonded via the aryl ketone photogroup to a surface --

Column 41,
Line 42, Claim 5, "composition comprising an" should be -- composition compromising a monomer compromising a --

Column 41,
Line 43, Claim 5, "ketone photogroup-derivatized monomer." should be -- ketone photogroup. --

Signed and Sealed this
Twenty-seventh Day of October, 2015

Michelle K. Lee
*Director of the United States Patent and Trademark Office*